US008257868B2

(12) United States Patent
Hagiwara et al.

(10) Patent No.: US 8,257,868 B2
(45) Date of Patent: Sep. 4, 2012

(54) MOLTEN SALT COMPOSITION AND USE THEREOF

(75) Inventors: Rika Hagiwara, Kyoto (JP); Kazuhiko Matsumoto, Kyoto (JP); Kenichiro Tamaki, Kyoto (JP); Toshiyuki Nohira, Kyoto (JP); Takuya Goto, Kyoto (JP)

(73) Assignee: Kyoto University, Kyoto-Shi, Kyoto (JP)

( * ) Notice: Subject to any disclaimer, the term of this patent is extended or adjusted under 35 U.S.C. 154(b) by 898 days.

(21) Appl. No.: 11/886,781

(22) PCT Filed: Mar. 22, 2006

(86) PCT No.: PCT/JP2006/305736
§ 371 (c)(1), (2), (4) Date: Jan. 21, 2009

(87) PCT Pub. No.: WO2006/101141
PCT Pub. Date: Sep. 28, 2006

(65) Prior Publication Data
US 2009/0212743 A1 Aug. 27, 2009

(30) Foreign Application Priority Data

Mar. 23, 2005 (JP) ................................. 2005-084801

(51) Int. Cl.
| | |
|---|---|
| *H01M 4/13* | (2010.01) |
| *H01M 6/18* | (2006.01) |
| *H01M 10/0562* | (2010.01) |
| *C07C 303/00* | (2006.01) |
| *C07C 307/00* | (2006.01) |
| *C07C 309/00* | (2006.01) |
| *C07C 311/00* | (2006.01) |
| *H01M 6/14* | (2006.01) |

(52) U.S. Cl. ................ 429/231.95; 429/231.4; 429/303; 429/304; 429/321; 564/80

(58) Field of Classification Search ............... 429/231.4, 429/231.95, 303, 312, 314, 321; 564/80
See application file for complete search history.

(56) References Cited

U.S. PATENT DOCUMENTS 4,303,748 A * 12/1981 Armand et al. ............... 429/312
(Continued)

FOREIGN PATENT DOCUMENTS

EP 0013199 * 7/1980
(Continued)

OTHER PUBLICATIONS

L. Xue et al, "Synthesis and structures of alkali metal salts . . . ;"Solid State Sciences. 4. 2002, pp. 1535-1545.
C. Roux et al, "Ionic behavior of alkaline complexes . . . " Electrochimica Acta, vol. 40, No. 8. 1995, pp. 953-957.
A. Ferry et al, "Transport Property and Raman Spectroscopic . . . "J. Electrochem. Soc., vol. 145, No. 5, May 1998, pp. 1586-1592.

*Primary Examiner* — Patrick Ryan
*Assistant Examiner* — Aaron Greso
(74) *Attorney, Agent, or Firm* — Harness, Dickey & Pierce, P.L.C.

(57) ABSTRACT

A molten salt composition is disclosed containing two or more types of molten salt MTFSI whose anion is an imide anion TFSI and whose cation is an alkali metal M exhibits a lower electrolyte melting point and a wider operating temperature range than a simple salt does. This brings about various advantages such as a wider range of materials that are chosen for use in batteries and the like.

11 Claims, 24 Drawing Sheets

U.S. PATENT DOCUMENTS

| | | | |
|---|---|---|---|
| 4,505,997 A | | 3/1985 | Armand et al. |
| 5,798,191 A | * | 8/1998 | Choquette et al. ....... 429/231.95 |
| RE37,805 E | * | 7/2002 | Choquette et al. ............ 429/303 |
| 2001/0021790 A1 | * | 9/2001 | Yonezawa et al. .............. 564/80 |

FOREIGN PATENT DOCUMENTS

| | | |
|---|---|---|
| JP | 58-225045 | 12/1983 |
| JP | 2003-282059 | 10/2003 |
| JP | 2003-331918 | 11/2003 |

* cited by examiner

A : PSEUDO REFERENCE
    ELECTRODE (Ag WIRE)
B : COUNTER ELECTRODE
    (GLASSY CARBON)
C : THERMOCOUPLE
D : WORKING ELECTRODE
    (GLASSY CARBON OR Ni WIRE)
E : ELECTROLYTE
F : GLASS CELL
G : HEATER

TG CURVE OF LiTFSI

TG CURVE OF NaTFSI

TG CURVE OF KTFSI

TG CURVE OF CsTFSI

DSC CURVE OF LiTFSI

DSC CURVE OF NaTFSI

DSC CURVE OF KTFSI

DSC CURVE OF CsTFSI

LiTFSI—NaTFSI

KTFSI—NaTFSI

NaTFSI—CsTFSI

LiTFSI−KTFSI

LiTFSI−CsTFSI

KTFSI—CsTFSI

FIG. 28

|  | LiTFSI | NaTFSI | KTFSI | CsTFSI |
|---|---|---|---|---|
| $T_d$ / K | 657 | 714 | 733 | 745 |

FIG. 29

|  | LiTFSI | NaTFSI | KTFSI | CsTFSI |
|---|---|---|---|---|
| $T_m$ / K | 506 | 530 | 469 | 395 |

FIG. 30

|  | LiTFSI-NaTFSI | LiTFSI-KTFSI | LiTFSI-CsTFSI |
|---|---|---|---|
| $T_{eu}$ / K | 453 | 423 | 385 |
| EUTECTIC COMPOSITION | $x_{NaTFSI} = 0.33$ | $x_{LiTFSI} = 0.43$ | $x_{LiTFSI} = 0.07$ |
|  | NaTFSI-KTFSI | NaTFSI-CsTFSI | KTFSI-CsTFSI |
| $T_{eu}$ / K | 453 | 383 | 394 |
| EUTECTIC COMPOSITION | $x_{NaTFSI} = 0.33$ | $x_{NaTFSI} = 0.07$ | - |

MOLTEN SALT COMPOSITION AND USE THEREOF

TECHNICAL FIELD

The present invention relates to molten salt compositions and uses therefor. Particularly, the present invention relates to a molten salt composition including two or more types of MTFSI whose cation is an alkali metal M and whose anion is an imide anion (TFSI), and to a use therefor.

BACKGROUND ART

Molten salts are salts that are in a molten state, and known examples of the molten salts cover a wide temperature range, i.e., vary from (i) slag melted at a high temperature to (ii) a room-temperature molten salt that liquefies at room temperature. Use of a molten salt as an electrolyte liquid makes it possible to cause an electrochemical reaction that is hard to cause with use of an aqueous electrolyte liquid, and various studies are currently under way in respective fields. Since molten salts can be given functionalities that vary depending on combinations of cations and anions, a wide variety of salts are currently under development for the purpose of various applications.

Known examples of anions that yield a salt having a relatively low melting point among those salts mentioned above include bis(trifluoromethylsulfonyl)amide anion (commonly called "imide anion", TFSI—, $N(SO_2CF_3)_2$—, after-mentioned chemical formula (1)). The history of the TFSI anion evolves from the 1990 report of Armand et al. on lithium bis(trifluoromethylsulfonyl)amide (LiTFSI). Since an electrolyte obtained by constructing a composite of LiTFSI and a polymer such as polyethyleneoxide (PEO) exhibits excellent properties as a lithium-ion secondary battery electrolyte, a large number of studies of the electrolyte as an electrolyte supporting salt have been under way up to the present date. Further, it is in 1996 that a room-temperature molten salt obtained by combining an imidazolium cation and a TFSI anion was reported.

In general, since a larger ion will have a larger Stokes radius, the mobility of an ion in a liquid tends to be low, so that conductivity becomes smaller. However, although a TFSI salt has a TFSI anion that is a relatively large anion, it exhibits a high conductivity. The reason for this is as follows: The TFSI anion has two highly electrically-negative $CF_3SO_2$ groups and contains charges nonlocalized on nitrogen atoms, and therefore becomes weakly associated with a cation, thereby causing an increase in ion concentration effective in charge transport. The same is equally true in cases where the TFSI anion is used as a counter anion of a room-temperature molten salt. For example, 1-ethyl-3-methyl-imidazolium bis(trifluoromethylsulfonyl)amide (EMImTFSI) exhibits a conductivity of 8.8 mS cm$^{-1}$ at room temperature. Furthermore, the TFSI salt also exhibits high electrochemical stability, and therefore is applied advantageously to the field of electrochemistry and expected to be applied as an electrolyte liquid for batteries and capacitors.

Meanwhile, salts MTFSI (M=Li, Na, K, Cs) each containing an alkali metal as a cation while similarly having a TFSI anion are solid at room temperature, but have a melting point in an intermediate temperature range (of not more than 300° C.). If the properties supposed to be exhibited by a TFSI anion in a room-temperature molten salt are preserved even in this temperature range, these MTFSI salts can be applied as an electrolyte useful in an intermediate temperature range, and can be expected to be applied to various fields of electrochemistry. However, although there have been reports on their crystal structures (LiTFSI, KTFSI, CsTFSI, LiTFSI.H$_2$O, NaTFSI.H$_2$O.MeOH) (see Non-patent Document 1), these salts have never been studied in detail as molten salts.

As described above, the application of LiTFSI as a lithium-ion secondary battery electrolyte supporting salt has been widely studied. However, the properties of simple LiTFSI as a molten salt have been hardly studied. Further, as with a composite of LiTFSI and a polymer, a composite of each of NaTFSI and KTFSI and a polymer has been examined; however, there are only a very small number of reports on NaTFSI and KTFSI (see Non-patent Documents 2 and 3). Further, there are no detailed reports on properties such as a melting point. As for CsTFSI, there are neither relevant studies nor reports on its properties, except for the aforementioned report on its crystal structure. Further, there are no reports on RbTFSI.

[Non-patent Document 1]
L. Xue, et al., Solid State Sciences 4 (2002) p 1535
[Non-patent Document 2]
C. Roux, H.-Y. Sanchez, Electrochim. Acta 40 (1995) p 953
[Non-patent Document 3]
A. Ferry, M. M. Doeff, L. C. Jonghe, Jelectro. Chem. 145 (1998) p 1586

DISCLOSURE OF INVENTION

As described above, a salt MTFSI whose cation is an alkali metal is considered for application to batteries and the like, and therefore is a material of great future potential. However, its properties have not been fully studied. Therefore, at present, the salt MTFSI is applied only in a limited way. Especially, in order to improve the usability with which the salt MTFSI is applied, it is essential to widen the operating temperature range. However, no such attempts have been reported.

In order to increase possible applications of MTFSI, there has been a strong demand for the development of a technique for widening the operating temperature range by lowering the melting point of an electrolyte. Further, not only the lowering of the melting temperature of an electrolyte but also the properties as to what metal or ceramics can be deposited are of great importance.

The present invention has been made in view of the foregoing problems, and it is an object of the present invention to provide (i) a technique, being capable of lowering the melting point of an electrolyte containing MTFSI or of depositing, layering, and eluting specific metal or ceramics with use of the electrolyte, which enables a wide range of applications of the electrolyte and (ii) a use therefor.

The inventors diligently studied in order to solve the foregoing problems. That is, the inventors synthesized alkali-metal imide salts MTFSI (M=Li, Na, K, Rb, Cs), and then evaluated the performance of the alkali-metal imide salts MTFSI as an electrolyte by examining the thermal and physical properties of the alkali-metal imide salts. The inventors also examined binary system phases, such as NaTFSI—LiTFSI, NaTFSI—KTFSI, NaTFSI—CsTFSI, and LiTFSI—KTFSI, most of which are centered on NaTFSI. As a result, the inventors newly found that the eutectic temperature of the eutectic composition of each of the binary systems is remarkably lower than the melting point of a simple salt, thereby completing the present invention. The present invention has been completed based on such new findings, and encompasses the following inventions:

(1) A molten salt composition containing two or more types of molten salt MTFSI whose anion is a substance TFSI represented by following chemical formula (I) and whose cation is an alkali metal M.

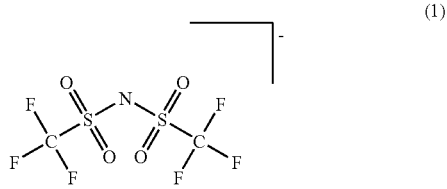

(2) The molten salt composition as set forth in (1), wherein the molten salt MTFSI is selected from the group consisting of LiTFSI, NaTFSI, KTFSI, RbTFSI, and CsTFSI.

(3) The molten salt composition as set forth in (1) or (2), wherein the molten salt composition is a binary system composition obtained by mixing two types of molten salt MTFSI, and is a LiTFSI—NaTFSI mixed system, a LiTFSI—KTFSI mixed system, a LiTFSI—CsTFSI mixed system, a NaTFSI—KTFSI mixed system, a NaTFSI—CsTFSI mixed system, or a KTFSI—CsTFSI mixed system.

(4) An electrolyte containing a molten salt composition as set forth in any one of (1) to (3).

(5) A battery containing an electrolyte as set forth in (4).

(6) The battery as set forth in (4), wherein the battery is used in a temperature range of 110° C. to 350° C.

(7) The battery as set forth in (6), wherein the battery is a lithium battery, a sodium-sulfur battery, or a zebra battery.

(8) A charging method comprising the step of performing charging with use of a battery as set forth in any one of (5) to (7).

(9) An electrodeposition method comprising the step of depositing metal or ceramics with use of an electrolyte as set forth in (4).

(10) A film-forming method comprising the steps of: depositing metal or ceramics with use of an electrolyte as set forth in (4); and forming a film on a surface of a substance with use of the metal or ceramics thus deposited.

(11) A surface-treating method comprising the steps of: depositing metal or ceramics with use of an electrolyte as set forth in (4); and treating a surface of a substance with use of the metal or ceramics thus deposited.

The molten salt composition according to the present invention has a eutectic temperature that is remarkably lower than the melting point of a simple salt containing only one type of MTFSI. Further, the range of temperatures at which the molten salt composition according to the present invention can be used can be widened by setting the composition and the proportions. For this reason, use of the molten salt composition according to the present invention makes it possible to lower the melting point of an electrolyte, thereby bringing about advantages in terms of energy efficiency and safety. Further, the widening of the operating temperature range brings about such an advantage as a wider range of materials that are chosen to be applied to batteries and the like.

Additional objects, features, and strengths of the present invention will be made clear by the description below. Further, the advantages of the present invention will be evident from the following explanation in reference to the drawings.

BRIEF DESCRIPTION OF DRAWINGS

FIG. 12($b$) is a diagram showing a result of cyclic voltammetry of LiTFSI in Examples of the present invention, which result is obtained when glassy carbon serves as an electrode.

FIG. 13($b$) is a diagram showing a result of cyclic voltammetry of NaTFSI in Examples of the present invention, which result is obtained when glassy carbon serves as an electrode.

FIG. 14($b$) is a diagram showing a result of cyclic voltammetry of KTFSI in Examples of the present invention, which result is obtained when glassy carbon serves as an electrode.

FIG. 15($b$) is a diagram showing a result of cyclic voltammetry of CsTFSI in Examples of the present invention, which result is obtained when glassy carbon serves as an electrode.

FIG. 16($b$) is a diagram showing an example of the DSC curves of the LiTFSI—NaTFSI mixed salt in Examples of the present invention, which example is obtained when $x_{NaTFSI}=0.70$.

FIG. 18($b$) is a diagram showing an example of the DSC curves of the KTFSI—NaTFSI mixed salt in Examples of the present invention, which example is obtained when $X_{NaTFSI}=0.70$.

FIG. 20(b) is a diagram showing an example of the DSC curves of the NaTFSI—CsTFSI mixed salt in Examples of the present invention, which example is obtained when $x_{NaTFSI}=0.70$.

FIG. 28 is a diagram showing the thermal decomposition temperature of each simple salt used in Examples of the present invention.

FIG. 29 is a diagram showing the melting point of each simple salt used in Examples of the present invention.

FIG. 30 is a diagram showing the eutectic composition and eutectic temperature of each of the mixed salts in Examples of the present invention.

BEST MODE FOR CARRYING OUT THE INVENTION

Figure 1:
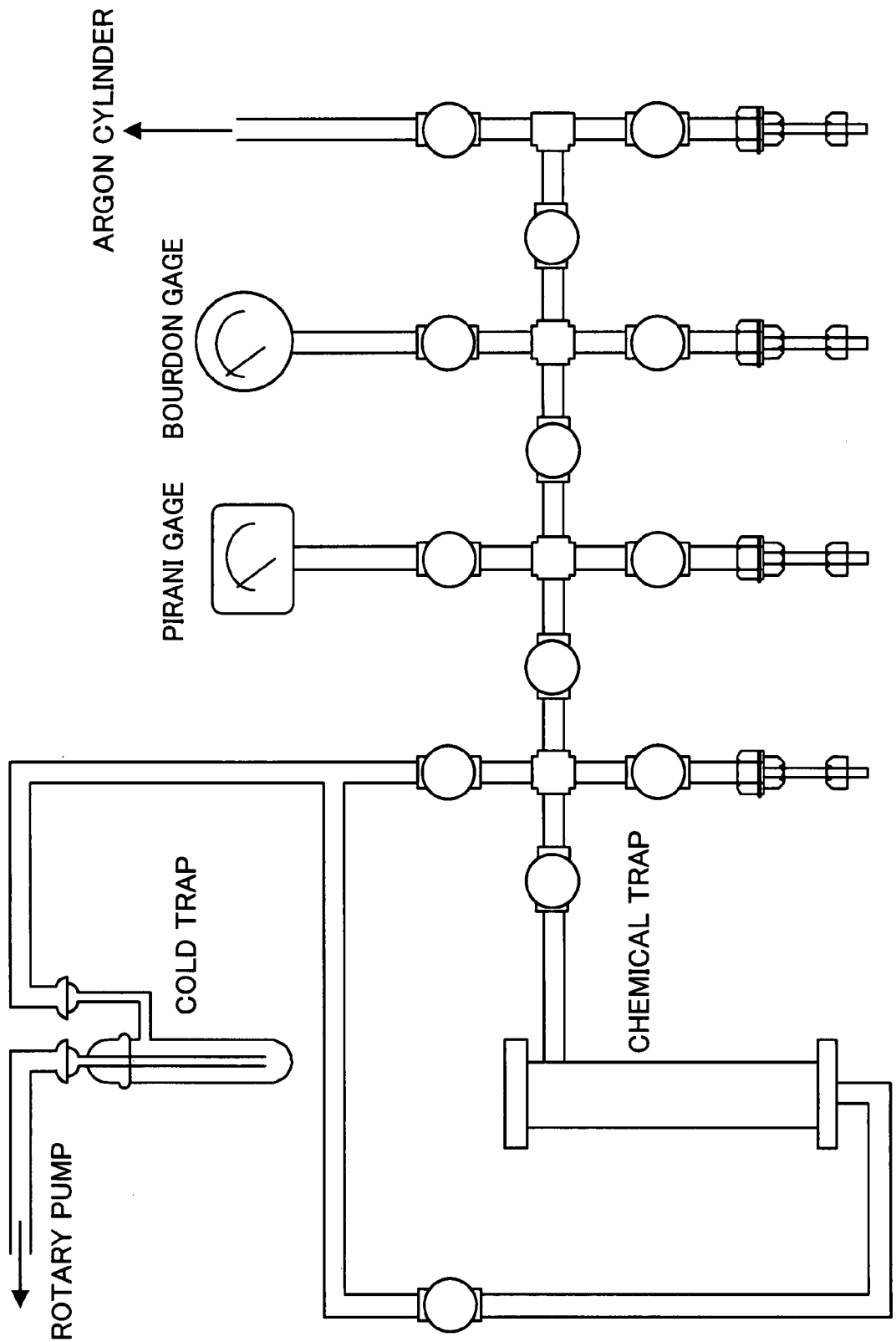
FIG. 1 is a diagram schematically showing an arrangement of an experimental apparatus used in Examples of the present invention.

In order to make it possible to apply MTFSI as an electrolyte at lower temperatures, the present invention has been obtained based on such results of the inventors' research that a mixed salt composition whose melting point is lower than the melting point of a simple salt can be obtained by mixing two or more types of alkali-metal imide salt (MTFSI). For this reason, a molten salt composition will be explained first, and then a use therefor will be explained.

Note that the term "imide" refers to an amide having an imino group. Strictly speaking, it is inappropriate to refer to a TFSI ion having no imino group as "imide". However, since the term is widely used today, it is used as a traditional term also in this specification.

<1. Molten Salt Composition>

A molten salt composition according to the present invention only needs to be a molten salt composition containing two or more types of molten salt MTFSI whose anion is a substance TFSI represented by the chemical formula (1) and whose cation is an alkali metal M, may contain any other substances within the scope of the object of the present invention, and is not particularly limited in terms of other specific arrangements and the like. The contained molten salts MTFSI are not particularly limited in terms of phase (solid, liquid), amount (proportion), and the like.

Since the molten salt composition according to the present invention is arranged to have two or more types of MTFSI as described above, it has such a characteristic quality that its melting point (eutectic temperature) is remarkably lower than the melting point of a simple salt. For this reason, the molten salt composition according to the present invention is excellent in terms of safety, corrosion control, energy cost, and the like. Further, the electrochemical properties and the melting temperature can be changed by adjusting the composition and the proportions of the molten salts that are mixed. This brings about such an advantage as to improve the degree of freedom to which an operating temperature, a material, and the like are chosen for a wide range of applications such as batteries.

Examples of the alkali metal M include lithium (Li), sodium (Na), potassium (K), rubidium (Rb), and cesium (Cs). For this reason, it is preferable that the molten salt MTFSI be selected from the group consisting of LiTFSI, NaTFSI, KTFSI, RbTFSI, and CsTFSI.

Among others, a composition containing two types of molten salt selected from the group consisting of LiTFSI, NaTFSI, KTFSI, RbTFSI, and CsTFSI, i.e., a so-called binary system composition is particularly preferable. Examples of the binary system composition include a LiTFSI—NaTFSI system, a LiTFSI—KTFSI system, a LiTFSI—CsTFSI system, NaTFSI—KTFSI system, a NaTFSI—CsTFSI system, and a KTFSI—CsTFSI system.

Among these binary system compositions, for example, the LiTFSI—KTFSI system and the LiTFSI—CsTFSI are preferable because they can be both applied to lithium batteries. Further, the NaTFSI—KTFSI mixed system and the NaTFSI—CsTFSI mixed system make it possible to deposit metallic sodium. Especially, in cases where an electrolyte for use in lithium batteries, sodium-sulfur batteries, and zebra batteries is considered as an application, the range of applications is further widened with such properties of the mixed systems that metal is easily deposited. Therefore, the evolution of technologies is expected.

Further, it is preferable that the molten salt composition be arranged to approximate to such a composition that a mixture of two or more types of molten salt forms a eutectic (eutectic composition). See examples of binary systems. It is preferable that the LiTFSI—NaTFSI system have a LiTFSI proportion of 0.1 to 0.6. Especially, it is preferable that the LiTFSI—NaTFSI system have a composition (eutectic composition) of $x_{LiTFSI}=0.33$ at which the eutectic temperature is lowest. Further, it is preferable that the LiTFSI—KTFSI system have a LiTFSI proportion of 0.2 to 0.8. Especially, it is preferable that the LiTFSI—KTFSI system have a composition (eutectic composition) of $x_{LiTFSI}=0.43$ at which the eutectic temperature is lowest. Further, it is preferable that the LiTFSI—CsTFSI system have a LiTFSI proportion of 0.03 to 0.7. Especially, it is preferable that the LiTFSI—CsTFSI system have a composition (eutectic composition) of $x_{LiTFSI}=0.07$ at which the eutectic temperature is lowest. Further, it is preferable that the NaTFSI—KTFSI system have a NaTFSI proportion of 0.05 to 0.6. Especially, it is preferable that the NaTFSI—KTFSI system have a composition (eutectic composition) of $x_{NaTFSI}=0.33$ at which the eutectic temperature is lowest. Further, it is preferable that the NaTFSI—CsTFSI system have a NaTFSI proportion of 0.03 to 0.6. Especially, it is preferable that the NaTFSI—KTFSI system have a composition (eutectic composition) of $X_{NaTFSI}$=0.07 at which the eutectic temperature is lowest.

As shown in Examples to be mentioned later, the eutectic temperature of the eutectic composition of each of the binary system compositions is as follows: The eutectic temperatures of the LiTFSI—NaTFSI system ($X_{NaTFSI}$=0.33), the LiTFSI—KTFSI system ($X_{LiTFSI}$=0.43), the LiTFSI—CsTFSI system ($X_{LiTFSI}$=0.07), the NaTFSI—KTFSI system ($X_{NaTFSI}$=0.33), the NaTFSI—CsTFSI system ($X_{NaTFSI}$=0.07), and the KTFSI—CsTFSI system were 453 K, 423 K, 385 K, 453 K, 383 K, and 394 K, respectively.

Further, the molten salt composition according to the present invention has a eutectic temperature that is changed by changing the composition and the proportions of the molten salts. Use of the properties makes it possible to set an optimum temperature range in accordance with an application by changing the composition and the proportions of the molten salts that are combined. This brings about such an advantage as a wider range of applications.

Especially, the molten salt composition according to the present invention can be used in a wide temperature range such as a low temperature range in which a conventional simple molten salt cannot be used and an intermediate to high temperature range in which the conventional simple salt can be used. Specifically, the molten salt composition according to the present invention can be used, for example, in a temperature range of 110° C. to 470° C.

As a molten salt that is used for the present invention, a conventionally publicly-known molten salt MTFSI whose cation is an alkali metal M and whose anion is a TFSI can be suitably used. Further, the molten salt can be prepared by a conventionally publicly-known method, and is not particularly limited in terms of specific means and the like for preparing the molten salt. However, for example, a method shown in Examples to be mentioned later can be used.

Thus, the molten salt composition according to the present invention has such a specific function and effect that the melting temperature (eutectic temperature) is lowered. For this reason, the molten salt composition according to the present invention is excellent in terms of safety, corrosion control, energy cost, and the like. That is, when a lowering of the melting temperature makes it possible to use a molten salt at low temperatures, it is possible to achieve a reduction in energy that is used for heating. Further, generally, most molten salts are likely to corrode material such as metal, and such properties become remarkable as a result of an increase caused in response speed in accordance with a rise in temperature. Therefore, if molten salts can be used at low temperatures, a reduction in progress of corrosion can be expected. If molten salts can be used at low temperatures, it will reduce the likelihood, for example, of an accident in which a high-temperature object leaks from a breakage or the like caused by material corrosion in apparatus material.

Further, when a molten salt is heated in excess of its melting point to reach its decomposition temperature, the molten salt becomes unable to maintain its chemical structure, thereby becoming unable to express the desired properties. For this reason, normally, a molten salt is used in a temperature range between its melting point and its decomposition temperature. The wider the temperature range between the melting point and the decomposition temperature is, the more operationality is improved. The molten salt composition according to the present invention has the same decomposition temperature as a simple salt while having a lower eutectic temperature than a simple salt does. This widens the temperature range between the melting point and the decomposition temperature, thereby bringing about such an advantage that operationality is improved.

As described above, the molten salt composition according to the present invention has various advantages as compared with a conventional molten salt and electrolyte. Especially, it can be said that the molten salt composition according to the present invention has advantages in terms of the following points. That is, a molten salt or ionic liquid that can be applied, for example, as an electrolyte liquid for use in lithium batteries and to electrodeposition of base metals at low temperatures must have a low melting point and a less noble reduction potential. However, an organic electrolyte obtained by dissolving a conventional electrolyte in an organic solvent or an imide salt ionic liquid containing an organic cation as a counter cation has a possibility that the organic solvent or the organic cation is decomposed at a higher potential before these metals are reduced and deposited. On the other hand, according to the present invention, an alkali-metal imide salt is used as a molten salt instead of being dissolved in an organic solvent, and plural types of molten salt are mixed. This makes it possible that the molten salt composition according to the present invention is used at a lower temperature than a simple salt is, thereby solving the foregoing problems.

<2. Use for the Molten Salt Composition>

Use of a molten salt as an electrolyte liquid makes it possible to cause an electrochemical reaction that is hard to cause with use of a system of aqueous solutions, and various types of research and development are currently under way for the purpose of various applications. For example, among various molten salts with various melting points, a salt with a melting point in an intermediate temperature range can be advantageously applied as an electrolyte for use in an electrochemical device that operates in an intermediate to high temperature range.

As described above, the present invention makes it possible to obtain a molten salt composition having a melting temperature that cannot be attained by a simple salt. That is, the molten salt composition according to the present invention has a melting temperature in an intermediate to high temperature range, therefore can be used especially in an intermediate to high temperature range. Therefore, for example, in the temperature range, an electrolyte liquid or electrolyte containing a molten salt composition as set forth in <1> can be used.

Further, the molten salt composition according to the present invention has a lower melting point (eutectic temperature) than a simple salt does, and therefore is vastly superior to a simple salt in terms of safety, room for selection of material, energy cost, and the like. For this reason, such advantages can be enjoyed even when a molten salt compound is used.

The electrolyte liquid or electrolyte is not particularly limited in terms of applications, and can be used for various products and techniques, known at the time of filing the subject application, which use an electrolyte.

The clause "the molten salt composition according to the present invention is used as an electrolyte liquid or electrolyte" here does not intend that the molten salt composition according to the present invention is used by dissolving it in a solvent, but intends that a molten salt obtained by melting a salt per se is directly used as an electrolyte liquid or electrolyte. Such a use is very preferable because it is not necessary to use a solvent. The reason for this is as follows: Because there are no volatility and inflammability due to the presence of a solvent, there are no such problems as ignition and explosion caused by depletion of an electrolyte liquid or a reaction with alkali metal.

That is, an alkali-metal imide salt, or a lithium salt in particular, has been considered for use as a supporting salt of an organic electrolyte liquid for use in lithium-ion batteries. The molten salt composition according to the present invention has excellent features in terms of the following points (i) to (v): (i) The molten salt composition according to the present invention does not contain an organic solvent; (ii) The molten salt composition according to the present invention is melted at a relatively low temperature; (iii) The molten salt composition according to the present invention is an alkali-metal imide salt serving as a low-temperature molten salt and a eutectic salt thereof; (iv) These salts are stable at a temperature that is higher than the melting temperature; and (v) alkali metal can be deposited in the molten salt.

These excellent features enable the molten salt composition according to the present invention to be used as an electrolyte liquid for use in various batteries, such as sodium-sulfur batteries, zebra batteries, and lithium secondary batteries (stationary, high output, for use in load leveling), which operate at lower temperatures. Especially, the molten salt composition according to the present invention brings about great advantages when used for a large-sized battery using an alkali-metal imide salt, e.g., can be used for charging night surplus electricity of a power plant or the like. Further, the molten salt composition according to the present invention can be used for a lithium secondary battery for use in an electric vehicle or a hybrid vehicle.

In cases where a large-sized lithium-ion battery is arranged with use of the molten salt composition according to the present invention, it is preferable that the molten salt composition according to the present invention be used in a temperature range in which generation of dendrite is inhibited. Specifically, it is preferable that the molten salt composition according to the present invention be used in a temperature range of 150° C. to 200° C. Whereas a conventional simple molten salt cannot be sufficiently used in this temperature range, the molten salt composition according to the present invention can be used in the temperature range.

Further, the present invention includes a charging method using a battery obtained with use of the molten salt composition. The charging method is not particularly limited in terms of specific techniques therefor as long as the battery is used, and the other steps, conditions, apparatuses, and the like may be conventionally publicly-known ones. The charging method enables efficient charging.

Note that it is obvious from the good conductivity of the molten salt composition according to the present invention that the molten salt composition can be used as an electrolyte.

Furthermore, the molten salt composition according to the present invention can be used as an electrolyte for use in electrodeposition or the like under such conditions that neither an aqueous solution nor a high-temperature molten salt can be used in a LIGA process or the like.

Further, in cases where the molten salt composition according to the present invention is used as a battery electrolyte, one alkali metal functions as a battery and the other alkali metal expresses a solvent-like function. That is, the molten salt composition according to the present invention is such that at least two types of alkali metal salt are mixed; therefore, the alkali metal that is more easily reduced by a negative electrode than the other is deposited first when electrolysis is performed by applying a voltage. Therefore, in cases where the molten salt composition according to the present invention is used as a battery electrolyte, the negative electrode of the battery becomes an electrode made of the alkali metal that is more easily reduced than the other.

Further, the molten salt composition according to the present invention was electrochemically measured to be found to exhibit such properties that an alkali metal constituting each simple salt is reduced and deposited. That is, an electrochemically base metal such as an alkali metal can be deposited. Use of such properties enables the molten salt composition according to the present invention to be used as a plating liquid in which a target metal that is less reducible than an alkali metal has been dissolved as a metal salt. Examples of such a target metal include alkaline-earth metals, rare-earth metals, high melting point metals of Groups 5 and 6.

Further, as will be shown later in Examples, it was confirmed by cyclic voltammetry that the molten salt composition according to the present invention has a cathodic limit at which an alkali metal or an alloy thereof is deposited. This can be said to show that alkali metals or the aforementioned various metals can be deposited without the occurrence of reductive decomposition of TFSI serving as an anion.

Therefore, an electrolyte liquid containing a molten salt composition according to the present invention can be used for an electrodeposition method, a film-forming method (plating), a surface-treating method, and the like.

An electrodeposition method according to the present invention only needs to use an electrolyte liquid containing the molten salt composition, and is not particularly limited in terms of other specific arrangements such as steps, conditions, and apparatuses. For example, the electrodeposition method according to the present invention only needs to be a method, using the molten salt composition as an electrolyte, which includes an electrodeposition step of depositing metal or ceramics by electrolysis of the electrolyte. The electrodeposition method can be suitably used for electroplating and the like.

Further, a film-forming method according to the present invention only needs to use an electrolyte liquid containing the molten salt composition, and is not particularly limited in terms of other specific arrangements such as steps, conditions, and apparatuses. The film-forming method is a method, using the molten salt composition as an electrolyte, which includes a wet process of depositing metal or ceramics by electrolysis of the electrolyte and covering a surface with the metal or ceramic. That is, the film-forming method is a so-called plating method. Examples of such a method include a method including at least the electrodeposition method and a step of covering a surface of a substance with the metal or ceramic deposited by the electrodeposition method. The film-forming method makes it possible to uniformly plate a surface of a substance. This makes it possible to obtain a plated object having a good surface finish.

Further, a surface-treating method according to the present invention only needs to use an electrolyte liquid containing the molten salt composition, and is not particularly limited in terms of other specific arrangements such as steps, conditions, and apparatuses. The surface-treating method only needs to be a method for treating a surface of a substance by using the molten salt composition as an electrolyte. Examples of the surface treatment include a surface treatment of an oxide film, a nitride film, a carbide film, a silicide film, and the like. As such, the surface-treating method brings about an effect of providing a surface with functions such as a high degree of hardness, abrasion resistance, and corrosion resistance.

The film-forming method or surface-treating method using an electrolyte liquid according to the present invention is not particularly limited in terms of a substance on which a film is to be formed or a substance whose surface is to be treated, but can be suitably performed by using, as a target object, a substance on which a film is to be formed by a film-forming method with use of a conventionally publicly-known electrolyte liquid or electrolyte or a substance whose surface is to be treated by a surface-treating method with use of a conventionally publicly-known electrolyte liquid or electrolyte. For example, a metal film or a ceramic film can be formed on a metal surface, an alloy surface, a ceramic surface, or a plastic surface; a metal surface or an alloy surface can be treated. For example, surfaces of jewelry goods, home electric appliances, and the like can be finished.

The embodiments of the present invention will be described more in detail below with reference to Examples. The present invention is not limited to the description of Examples below, and details of the present invention can be in various modes. The present invention is not limited to the description of the embodiments above, but may be altered by a skilled person within the scope of the claims. An embodiment based on a proper combination of technical means disclosed in different embodiments is encompassed in the technical scope of the present invention.

EXAMPLES (1) Experiment (1-1) Experimental Apparatus

Since most of the chemicals used in Examples easily react with moisture contained in the air, they were treated in a deoxygenated and dehydrated glove box, provided with a gas purifier, which is in an argon atmosphere. For the purpose of controlling the moisture contained in the box, the moisture contained in the ambient gas was always monitored by a dew point meter. In the glove box, an electronic even balance was installed so that the reagents can be weighed.

FIG. 1 shows a corrosion-resistant reaction line used for the experiment. The main body was composed of pipes (each having an outer diameter of ½ inch) made of stainless steel SUS316 that is excellent in terms of corrosion resistance. Those pipes were connected to one another by using a swage lock together with a joint, an SUS316 stainless-steel vacuum valve (Whitey) using a Kel-F tip, and the like. Connected to the reaction line was an oil rotary vacuum pump in front of which a glass cold trap was installed. By cooling the cold trap with liquid nitrogen, water and corrosive gases were prevented from entering the pump. Corrosive gases such as fluorine and fluoride gases were removed roughly via a chemical trap using soda lime. Since the chemical trap causes a large pressure drop and does not yield a high degree of vacuum, the air was discharged directly from the valve without passing through the chemical strap. The line has a maximum degree of vacuum in the order of approximately $10^{-2}$ Torr.

(1-2) Reagents

Commercially-available HTFSI (Morita Chemical Industries Co., Ltd.; not less than 99.0%), LiTFSI (Morita Chemical Industries Co., Ltd.; not less than 99.0%), $Na_2CO_3$ (Wako Pure Chemical Industries, Ltd.; 99.5%), $K_2CO_3$ (Wako Pure Chemical Industries, Ltd.; 99.9%), and $Cs_2CO_3$ (Aldrich; 99.9%) were directly used. A commercially-available ethanol (Wako Pure Chemical Industries, Ltd.; 99%) was directly used as a reaction solvent.

(Synthesis)

Figure 2:
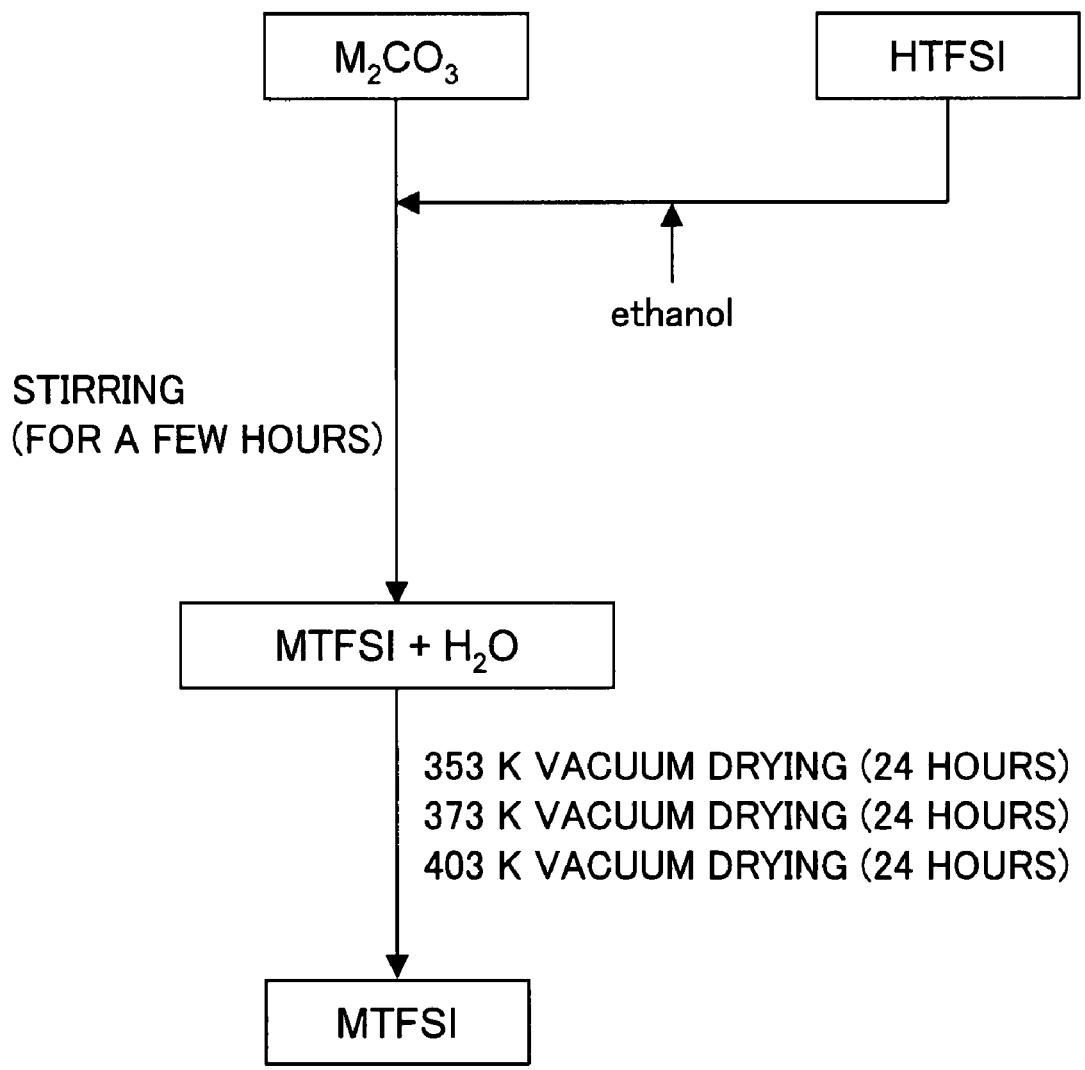
FIG. 2 is a diagram showing a procedure for synthesizing a molten salt in Examples of the present invention.

FIG. 2 shows a procedure for synthesizing MTFSI (M=Li, Na, K, Cs). MTFSI was synthesized according to the following reaction formula:

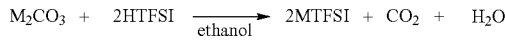

$M_2CO_3$ and HTFSI were weighed in the glove box. Thereafter, ethanol was added as a reaction solvent to HTFSI in a draft, and then HTFSI was allowed to react with $M_2CO_3$. In so doing, in order that neither $M_2CO_3$ nor HTFSI became excessive, neutralization was performed while sequentially checking the pH of the solution with use of pH-test paper. Thereafter, the ethanol was roughly removed by stirring the solution for a few hours with a rotary evaporator. The resulting product was poured into a quartz glass tube, and then was dried by performing vacuuming at 353 K for 24 hours, at 373 K for 24 hours, and then at 403 K for 24 hours. As a result, white powder was obtained.

(1-3) Analysis (1-3-1) Thermal Analysis

As thermal analysis, thermogravimetry and differential scanning calorimetry were performed.

The thermogravimetry was performed with use of a simultaneous differential calorimetric and thermogravimetric apparatus (Shimadzu Corporation, DTG-60/60H). The aluminum cell used was washed with ethanol and distilled water before measurement, and then was sufficiently dried. A sample was placed into the aluminum cell. The scan rate was 10 $Kmin^{-1}$. The measurements were performed in an atmosphere of nitrogen gas. Since LiTFSI has deliquescent properties, the measurement was performed after raising its temperature to 573 K in order to remove moisture. As for NaTFSI, KTFSI, and CsTFSI, the measurements were performed without changing them.

The differential scanning calorimetry was performed with use of a differential scanning calorimeter (Shimadzu Corporation, DSC60). A cell made of aluminum was used. A sample was placed into the cell in the glove box that was in an argon atmosphere, and the cell was sealed with a sealer/crimper (Shimadzu Corporation, SSC-30), and then was subjected to measurement. The scan rate was 10 $Kmin^{-1}$. The measurements were performed in an atmosphere of nitrogen gas. The differential scanning calorimetry of a mixture of NaTFSI and another salt was performed by changing the NaTFSI mole percentage $x_{NaTFSI}$ from 0.05 to 0.95 by 0.05. The mixture was heated to 533 K, and then was cooled to room temperature. The measurement was performed after further heating the mixture to 553 K.

(1-3-2) Electrochemical Measurement

Figure 3:
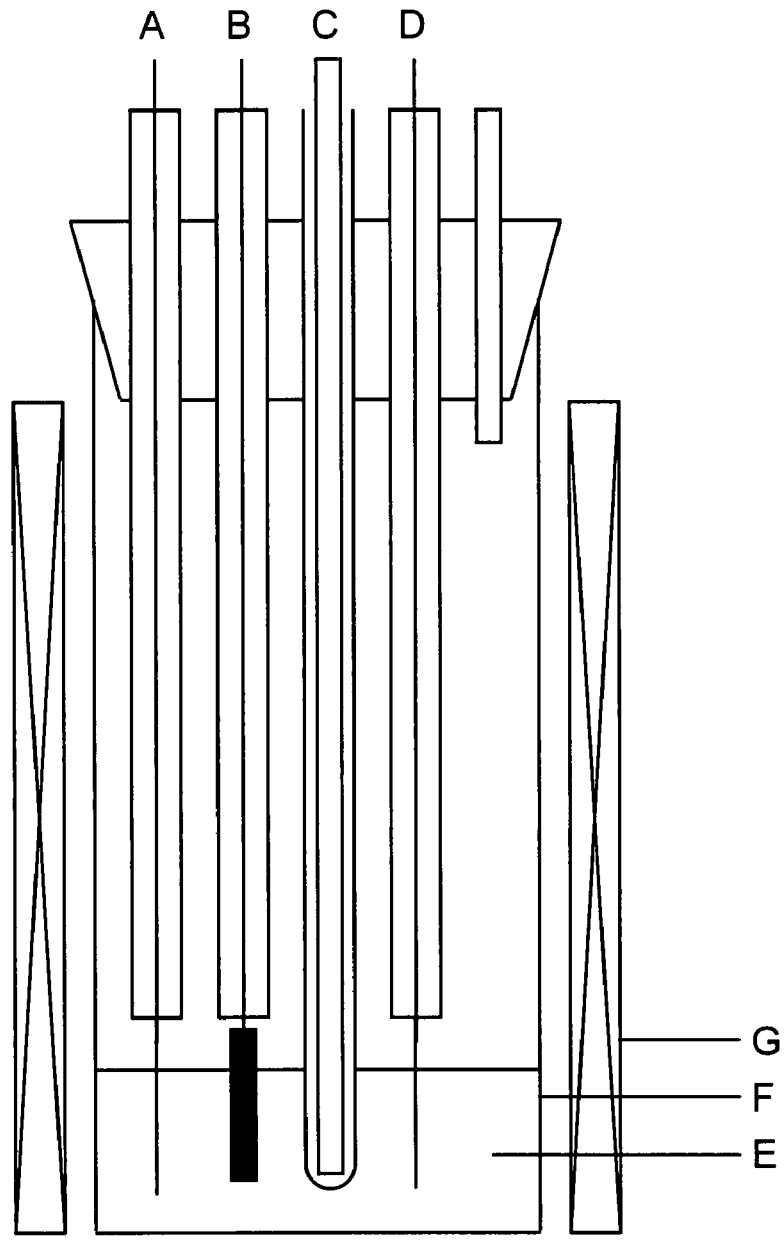
FIG. 3 is a diagram showing an electrochemical measuring apparatus used in Examples of the present invention.
Figure 4:
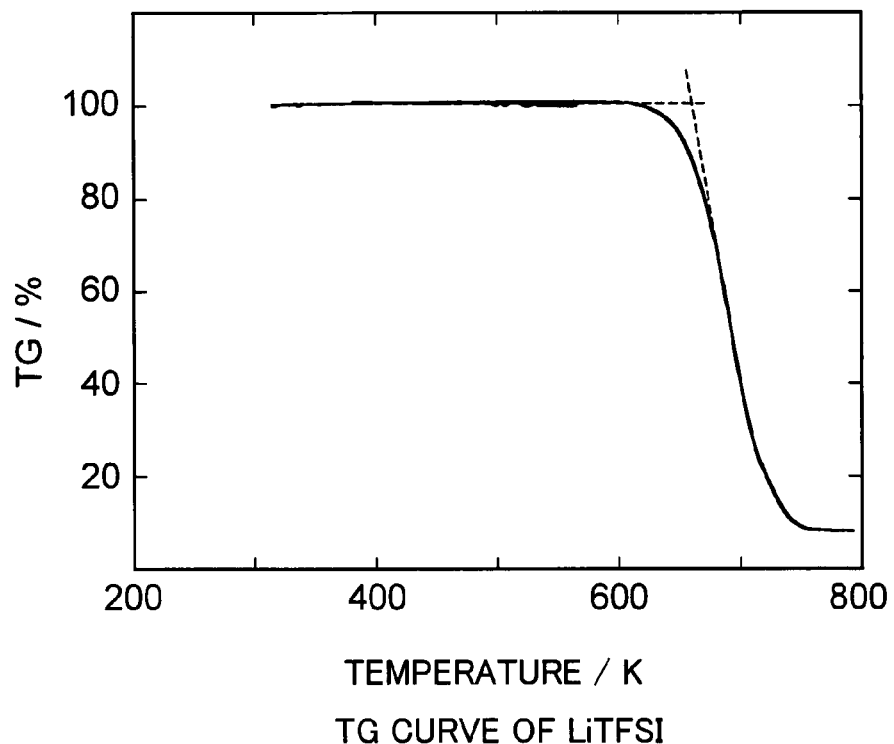
FIG. 4 is a diagram showing a TG curve of LiTFSI in Examples of the present invention.
Figure 5:
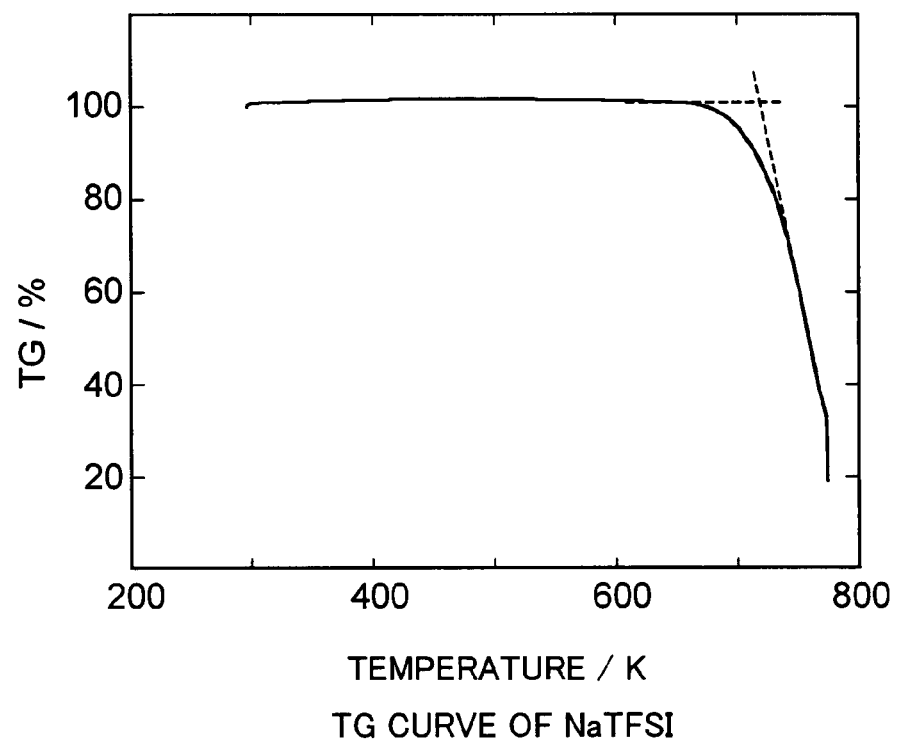
FIG. 5 is a diagram showing a TG curve of NaTFSI in Examples of the present invention.
Figure 6:
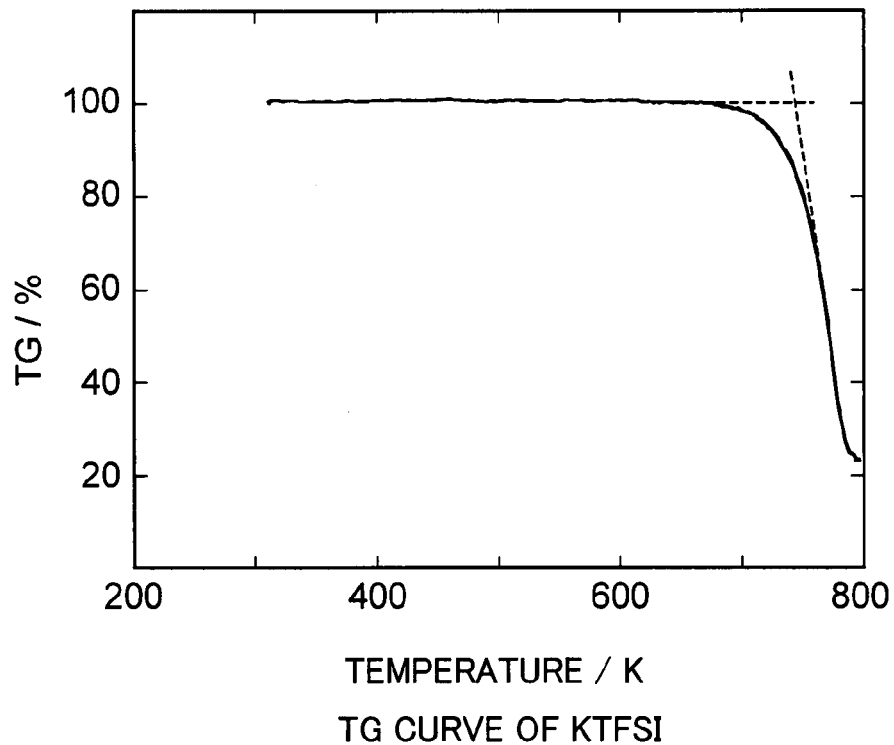
FIG. 6 is a diagram showing a TG curve of KTFSI in Examples of the present invention.
Figure 7:
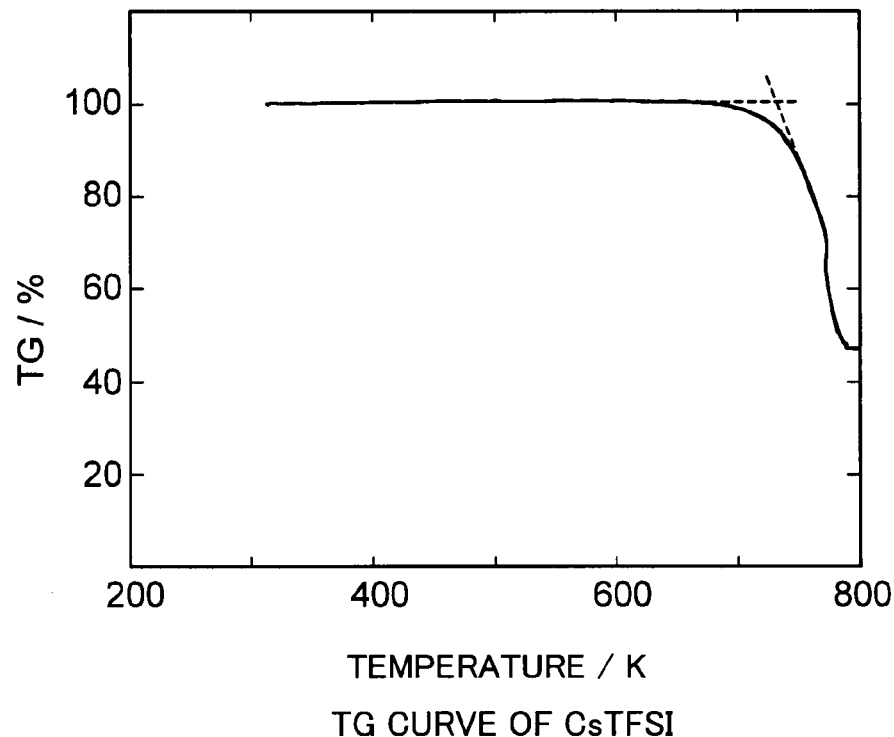
FIG. 7 is a diagram showing a TG curve of CsTFSI in Examples of the present invention.
Figure 8:
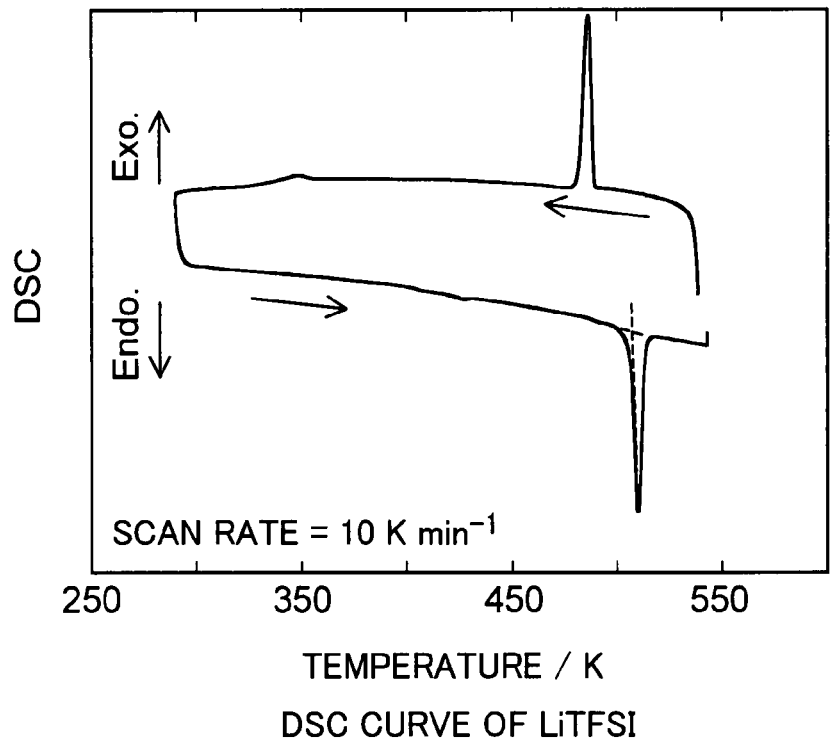
FIG. 8 is a diagram showing a DSC curve of LiTFSI in Examples of the present invention.
Figure 9:
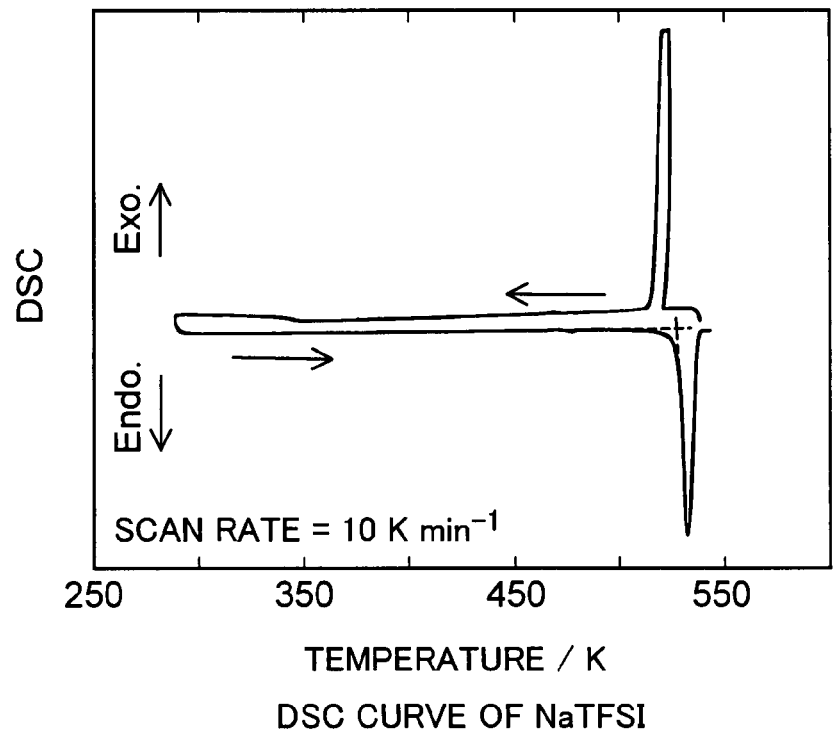
FIG. 9 is a diagram showing a DSC curve of NaTFSI in Examples of the present invention.
Figure 10:
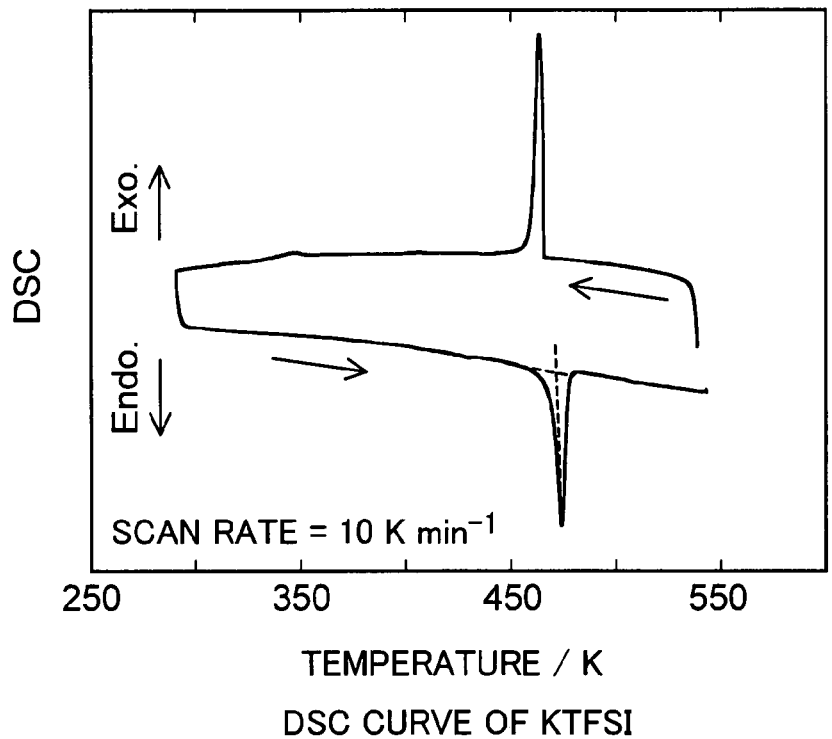
FIG. 10 is a diagram showing a DSC curve of KTFSI in Examples of the present invention.
Figure 11:
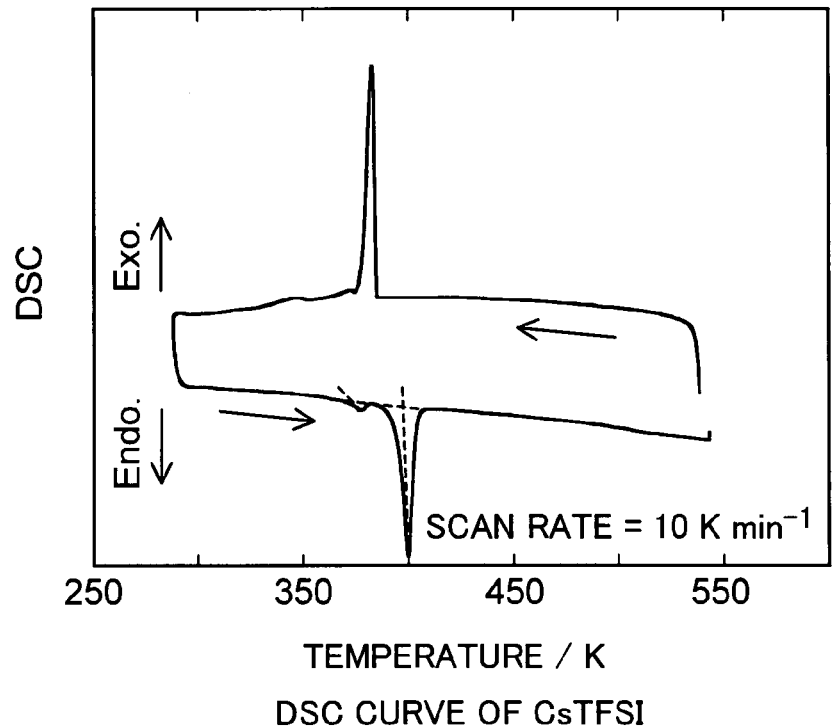
FIG. 11 is a diagram showing a DSC curve of CsTFSI in Examples of the present invention.
Figure 12:
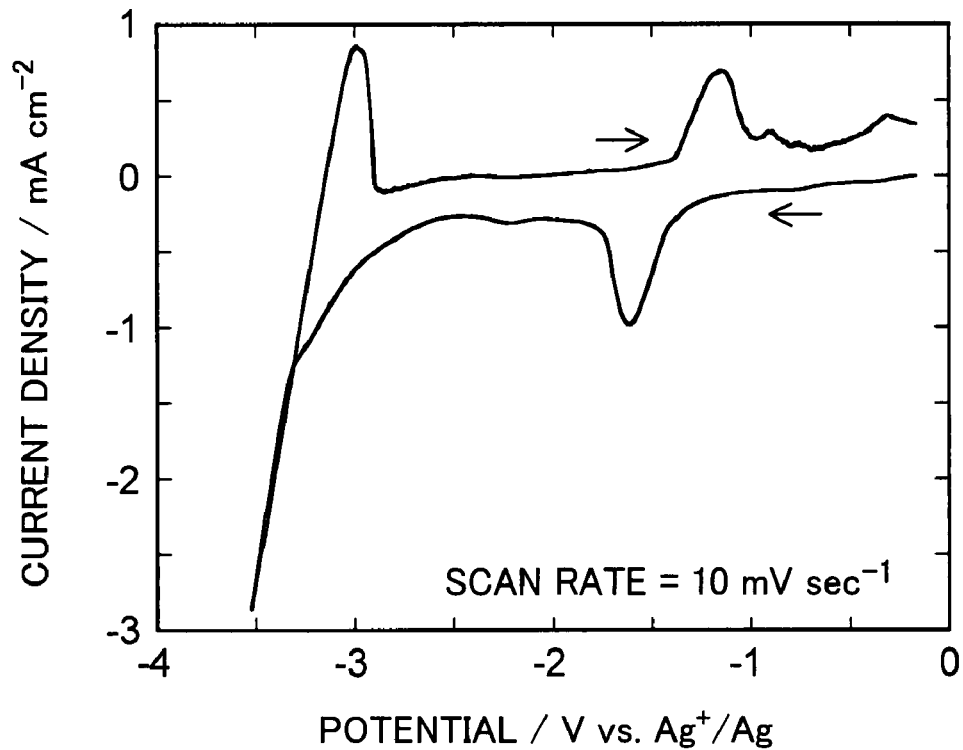
FIG. 12($a$) is a diagram showing a result of cyclic voltammetry of LiTFSI in Examples of the present invention, which result is obtained when Ni serves as an electrode.
Figure 12:
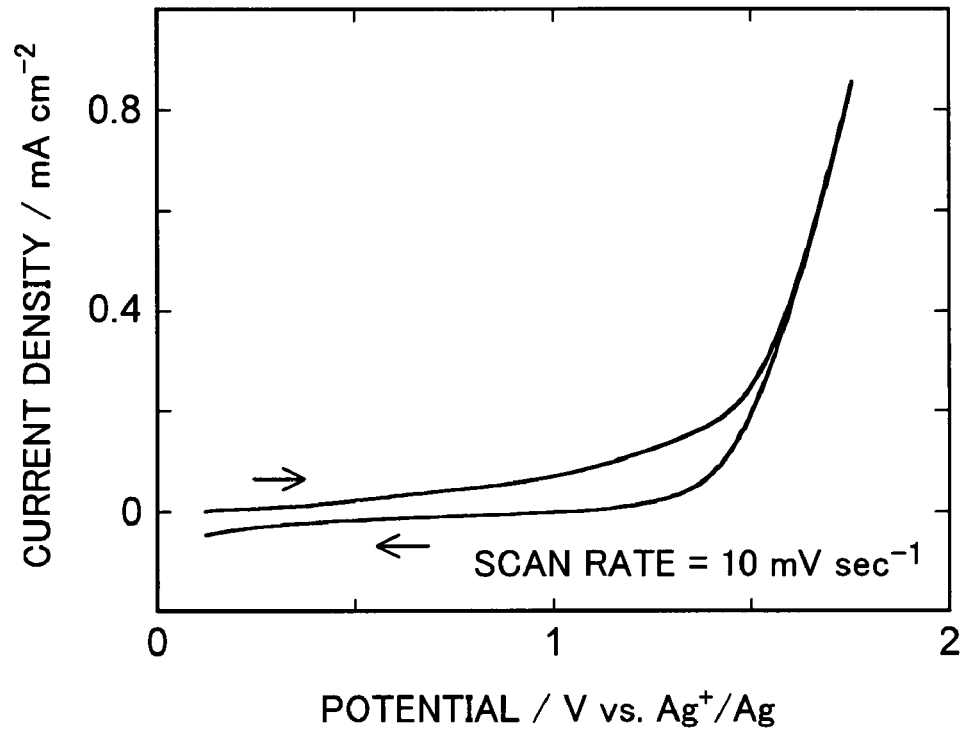
Figure 13:
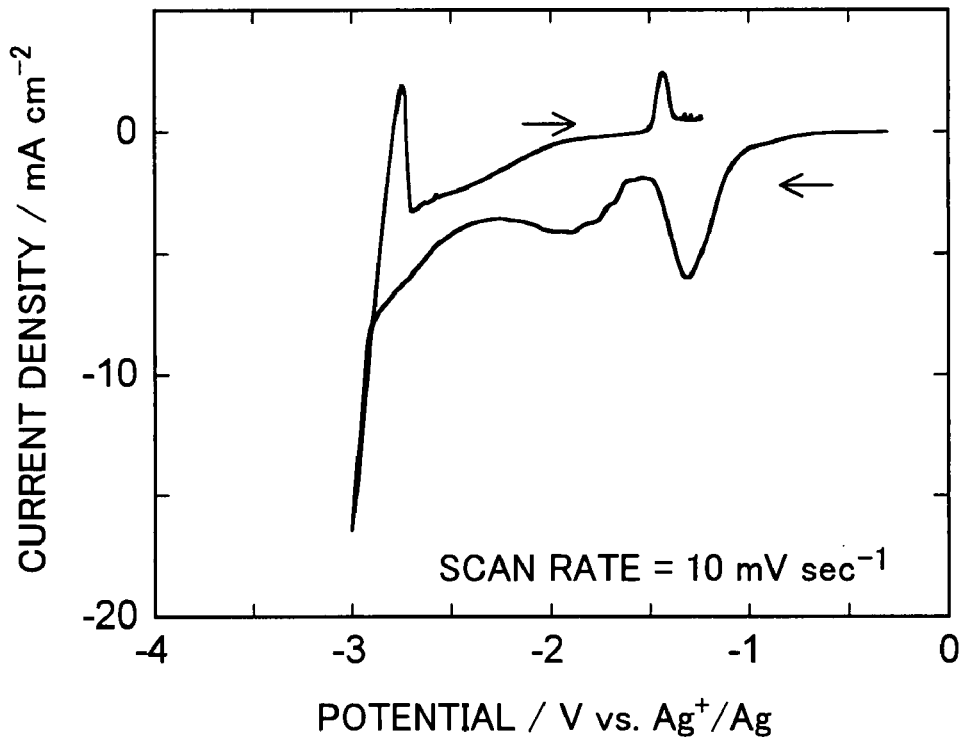
FIG. 13($a$) is a diagram showing a result of cyclic voltammetry of NaTFSI in Examples of the present invention, which result is obtained when Ni serves as an electrode.
Figure 13:
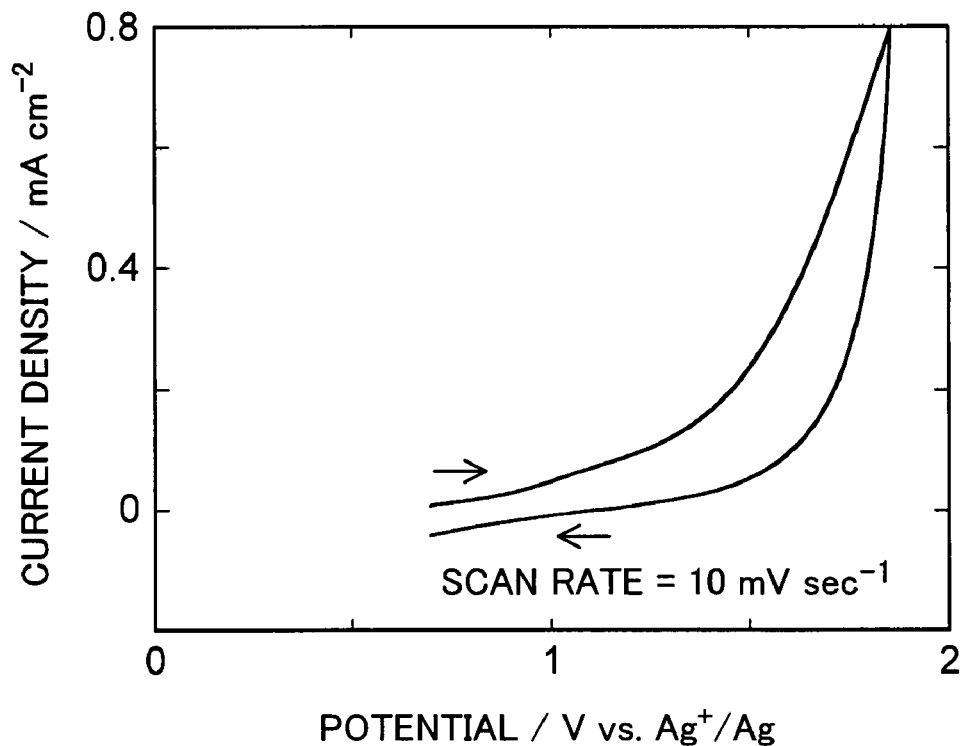
Figure 14:
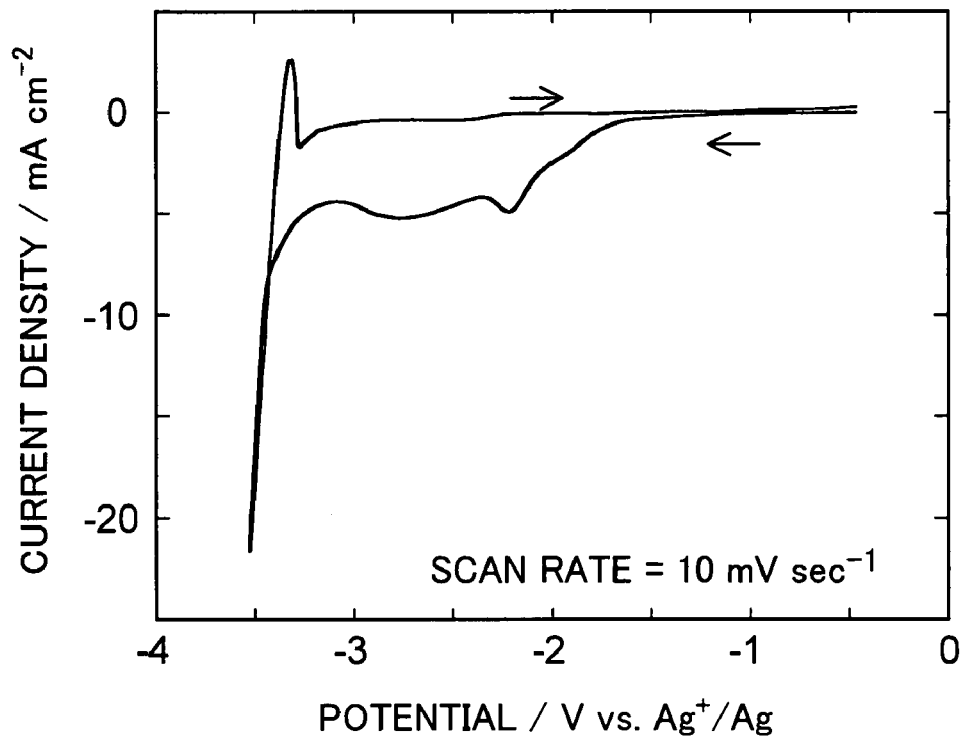
FIG. 14($a$) is a diagram showing a result of cyclic voltammetry of KTFSI in Examples of the present invention, which result is obtained when Ni serves as an electrode.
Figure 14:
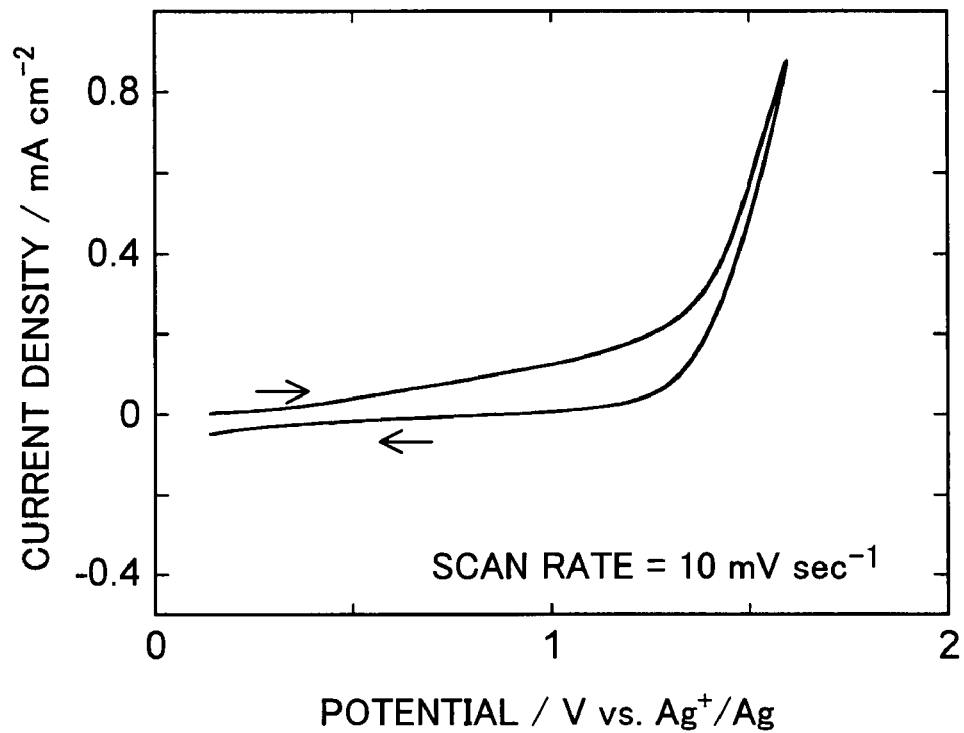
Figure 15:
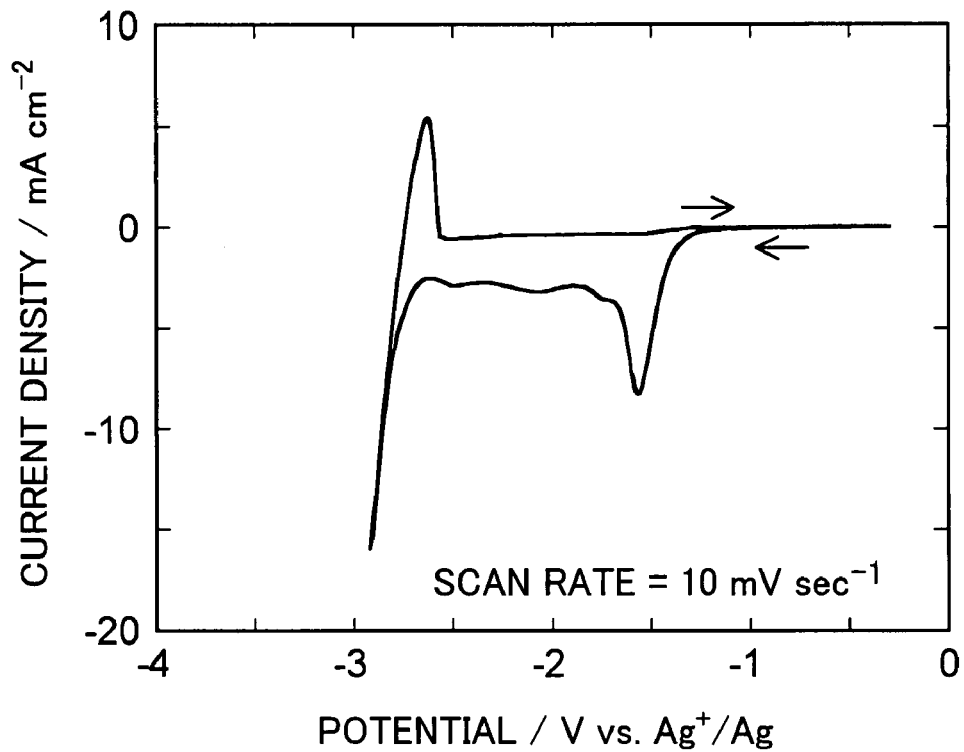
FIG. 15($a$) is a diagram showing a result of cyclic voltammetry of CsTFSI in Examples of the present invention, which result is obtained when Ni serves as an electrode.
Figure 15:
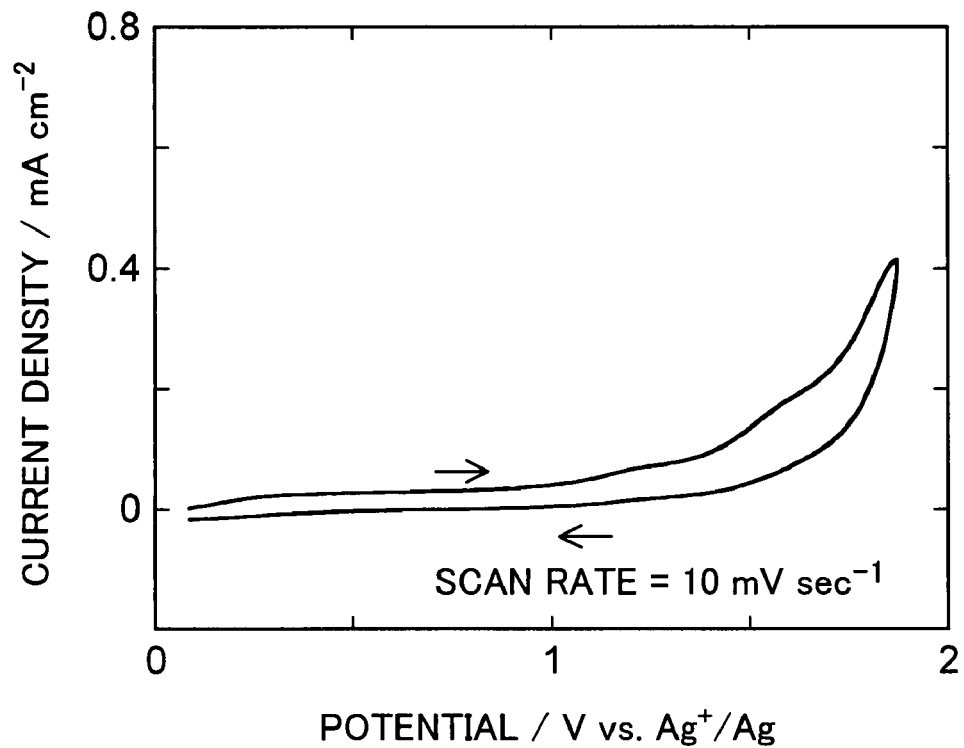

The electrochemical measurement was performed with use of an electrochemical measuring apparatus HZ-3000 (Hokuto Denko Corporation). The cyclic voltammetry was performed with use of a cell made of glass. A nickel wire or a glassy carbon rod was used as a working electrode. A glassy carbon rod was used as a counter electrode. A silver wire was used as a pseudo-reference electrode. FIG. 3 shows a pattern diagram of the measuring apparatus. The measurement was performed in the glove box that was in an argon atmosphere. In so doing, the bath temperature was kept higher by approximately 30 K with use of a heater than the melting point of the salt.

(2) Results and Reviews (2-1) Simple Salts MTFSI

Thermal Properties

FIGS. 4 to 7 show respective TG curves of the simple salts MTFSI. The thermal decomposition temperature was determined by taking a point of contact between the baseline and a TG curve obtained after weight reduction. FIG. 28 shows the thermal decomposition temperature of each of the simple salts. It was found that as the size of a cation becomes larger, the thermal decomposition temperature tends to become higher. This coincides with such thermal stability of a typical ionic crystal that a large cation stabilizes a large anion.

Figure 23:
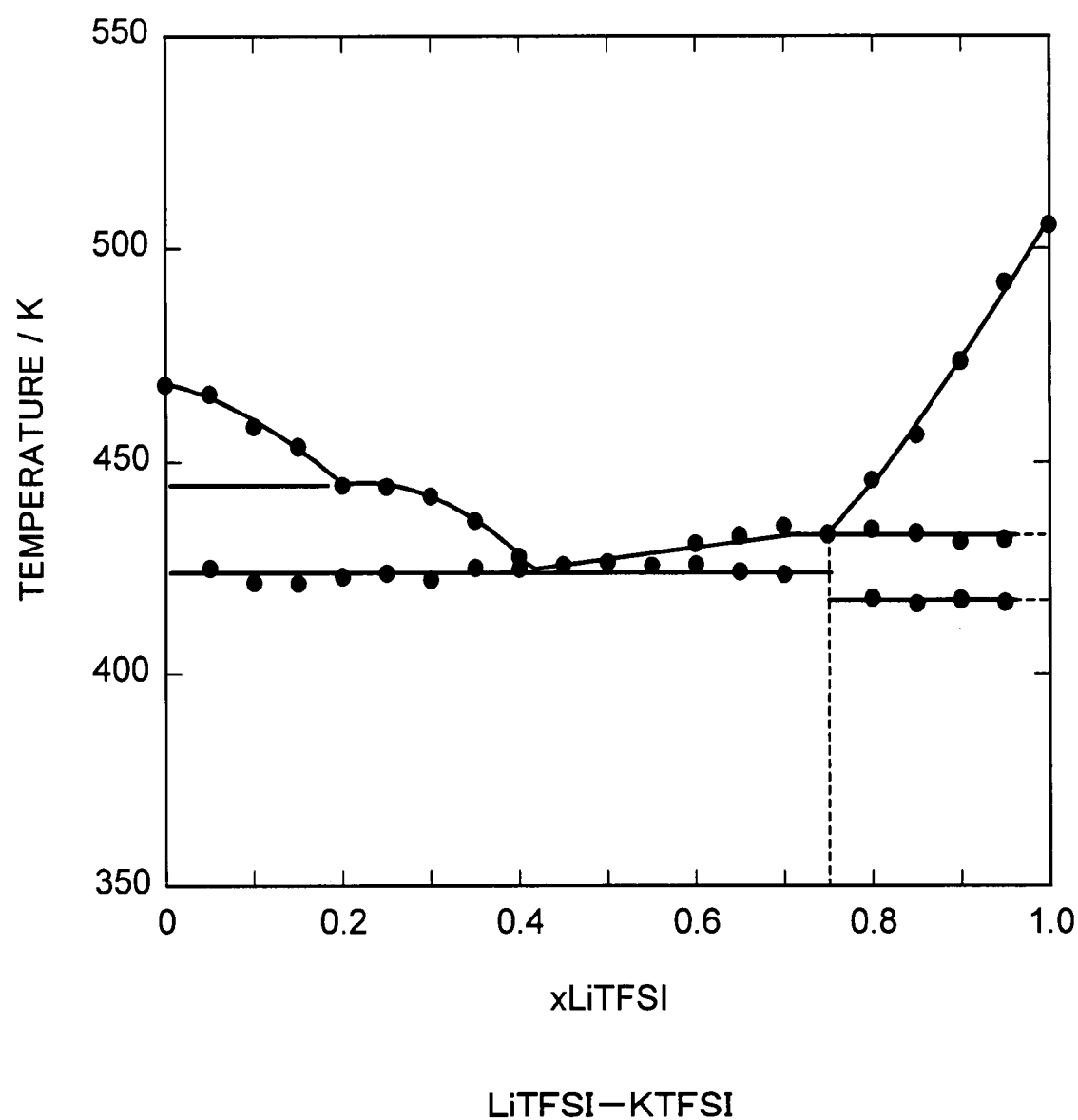
FIG. 23 is a binary system phase diagram prepared by plotting endothermic peaks of the LiTFSI—KTFSI mixed salt in Examples of the present invention.

FIGS. 8 to 11 show respective DSC curves of the simple salts MTFSI. The melting point was determined by taking a point of contact between a line extending from the baseline and a line tangent to the endothermic peak. FIG. 23 shows the melting point of each of the simple salts. Unlike the tendency of the thermal decomposition temperature, it was found that NaTFSI has the highest melting point of all the simple salts. In the DSC curve of CsTFSI, a small endothermic peak was found near 373 K. The peak is considered to correspond to the evaporation of a slight amount of water that had not been removed by vacuum drying. However, such a possibility is low in consideration of the fact that the salt had been dried in vacuum for 3 days. The peak may also be considered to correspond to a phase transition. However, no details have been found.

(2-1-2) Electrochemical Properties

FIGS. 12(a) to 15(b) show results of cyclic voltammetry of the simple salts MTFSI, respectively. A nickel wire was used as a working electrode for sweeping the potential in a less noble direction. A reduction current started to flow at approximately −1.2 V, and constantly flowed afterward. Thereafter, peaks were found which are considered to respectively correspond to the deposition and dissolution of the alkali metal. In the cases of LiTFSI and NaTFSI, an oxidation current was found near −1.5 V after the turn of the potential. After the measurement, a black substance was found to have adhered to a surface of the nickel wire. Even a repetition of the measurement resulted in the same voltammograph.

No details have been found yet as to what caused such a reduction current at a more noble potential than the alkali metal deposition. However, the reduction of the TFSI anion is quite unlikely to be the cause, because the TFSI anion has very strong resistance to reduction at normal temperature. Another possible cause is contamination by impurities such as (i) HTFSI serving as a material for the salts, (ii) alkali metal carbonate, and (iii) water, generated at the time of synthesis, which was not able to be removed by vacuum drying. However, since the pH of an aqueous solution of each salt was neutral, it is hard to believe that the salt had been contaminated by HTFSI or carbonate. Except for CsTFSI, no such an endothermic peak was found on the DSC curve as to correspond to the evaporation of water. Furthermore, the same results were produced even when the salt had been subjected to bubbling with argon for 24 hours before measurement. Therefore, water is quite unlikely to be the cause. Another possible cause is the contamination of a surface of the electrode or the influence of an oxide layer. However, in consideration of the fact that the reduction current peak obtained by directly using commercially-available LiTFSI is smallest, there seems to be a problem with the bath rather than the electrode. Further, it is conceivable that the decomposition of the TFSI anion is facilitated due the existence of such a slight amount of water in the bath that cannot be found on the DSC curve. There are various possible causes as described above. In this respect, further detailed consideration is required. If the cause of the reduction current is not the properties of the salt but the influence of the impurities, it can be said that MTFSI has a very wide potential window in a less noble direction.

A glassy carbon rod was used as a working electrode for sweeping the potential in a noble direction. In each case, a peak of oxidation current was found near 1.8 V. This is considered to correspond to the oxidation of the TFSI anion, and is approximately consistent with the oxidation potential of a TFSI anion of a TFSI-system molten salt that is at normal temperature (see H. Matsumoto, Molten Salt XII, edited by P. C. Trulove et al., *Electrochem. Soc.*, Pennington, N.J., (2000) p. 186.). However, the fact that the current gradually flowed even in a potential region before the peak implied a possibility that some sorts of impurities were contained in the bath.

(2-2) Binary System Molten Salts (2-2-1) Binary System Phase Diagrams

Figure 16:
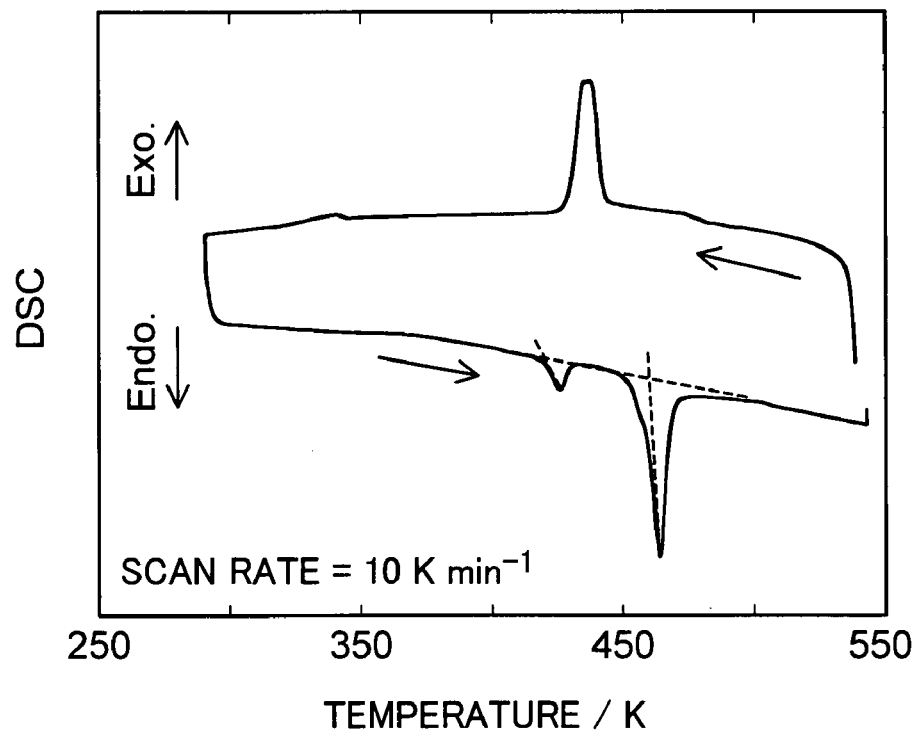
FIG. 16($a$) is a diagram showing an example of DSC curves of a LiTFSI—NaTFSI mixed salt in Examples of the present invention, which example is obtained when $x_{NaTFSI}=0.35$.
Figure 16:
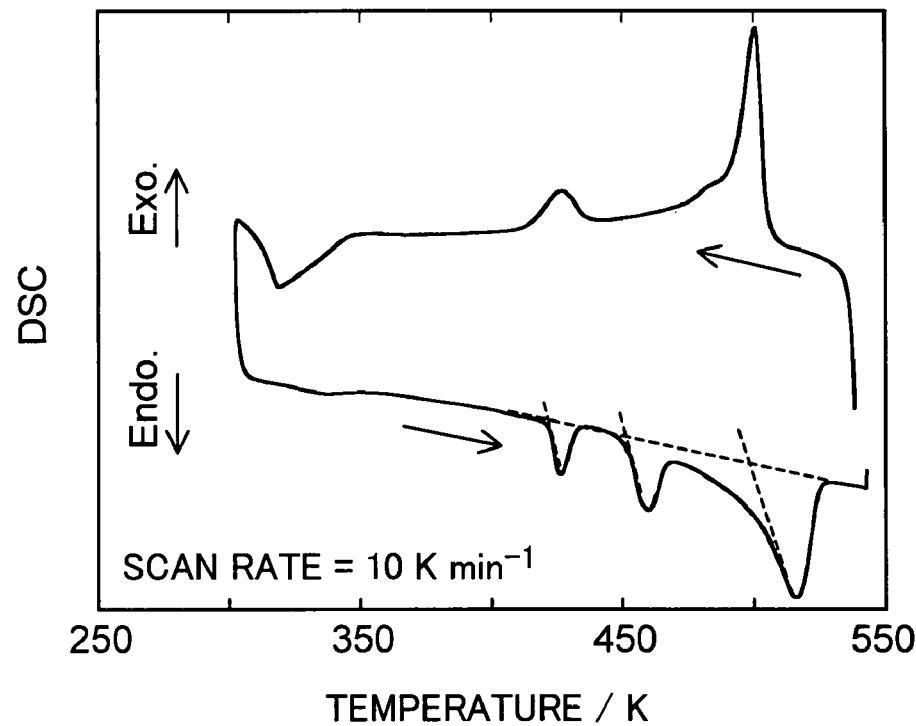
Figure 17:
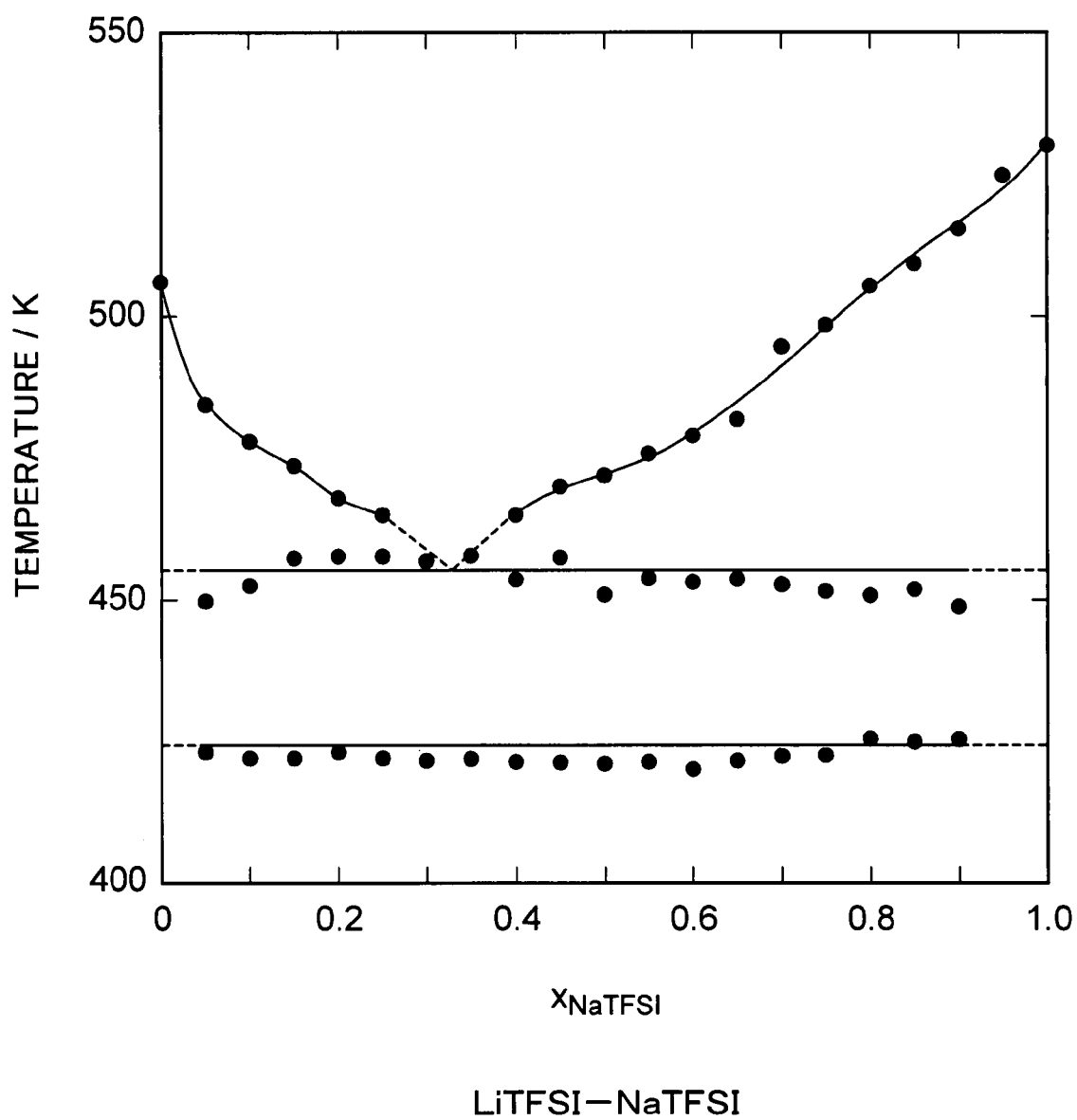
FIG. 17 is a binary system phase diagram prepared by plotting endothermic peaks of the LiTFSI—NaTFSI mixed salt in Examples of the present invention.

In an effort to lower the melting point of a salt, phase diagrams were prepared with respect to binary system mixed salts, such as LiTFSI—NaTFSI, KTFSI—NaTFSI, and NaTFSI—CsTFSI, most of which are centered on NaTFSI. First, the LiTFSI—NaTFSI system is shown. FIG. 16(a) shows an example of a DSC curve of the LiTFSI—NaTFSI mixed salt, which example is obtained when $x_{NaTFSI}$=0.35. FIG. 16(b) shows an example of the DSC curve of the LiTFSI—NaTFSI mixed salt, which example is obtained when $x_{NaTFSI}$=0.70. FIG. 17 shows a binary system phase diagram prepared by plotting endothermic peaks of these examples. It was found that the eutectic composition was $x_{NaTFSI}$=0.33 and the eutectic temperature was approximately 453 K.

In addition to the endothermic peak considered to correspond to the melting, another endothermic peak was found near 423 K. The endothermic peak became smaller as $x_{NaTFSI}$ became larger, and was not able to be found on DSC curves respectively obtained when $X_{NaTFSI}$=0.90 and $X_{NaTFSI}$=0.95. From these results, it is considered that the endothermic peak is derived from LiTFSI and corresponds to a phase transition of the mixed salt. However, no details have been found thereabout.

Figure 18:
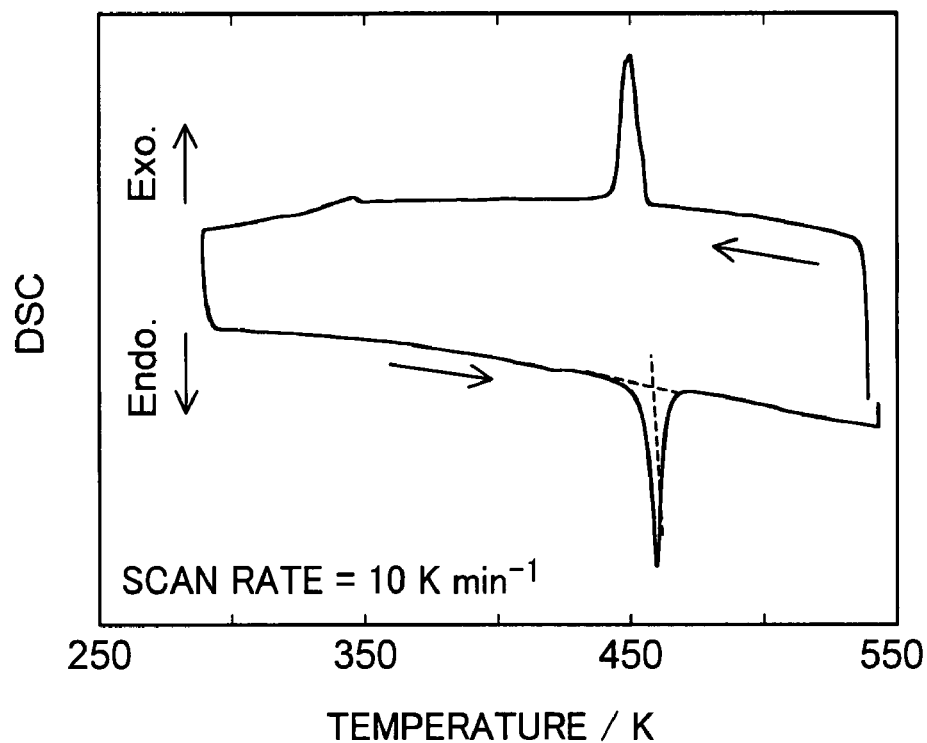
FIG. 18($a$) is a diagram showing an example of DSC curves of a KTFSI—NaTFSI mixed salt in Examples of the present invention, which example is obtained when $x_{NaTFSI}=0.35$.
Figure 18:
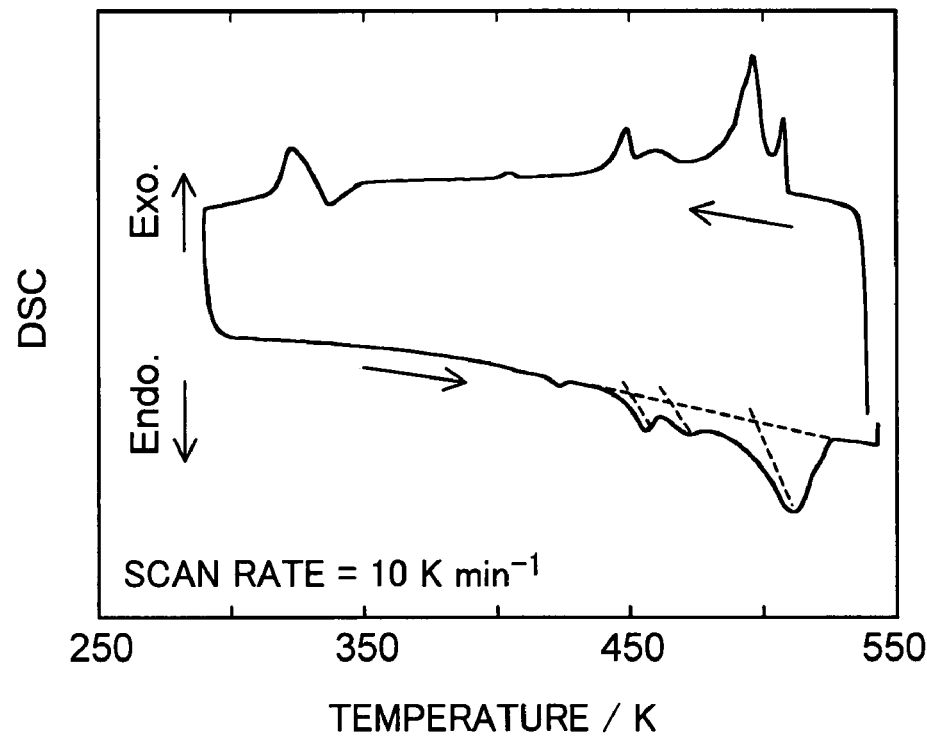
Figure 19:
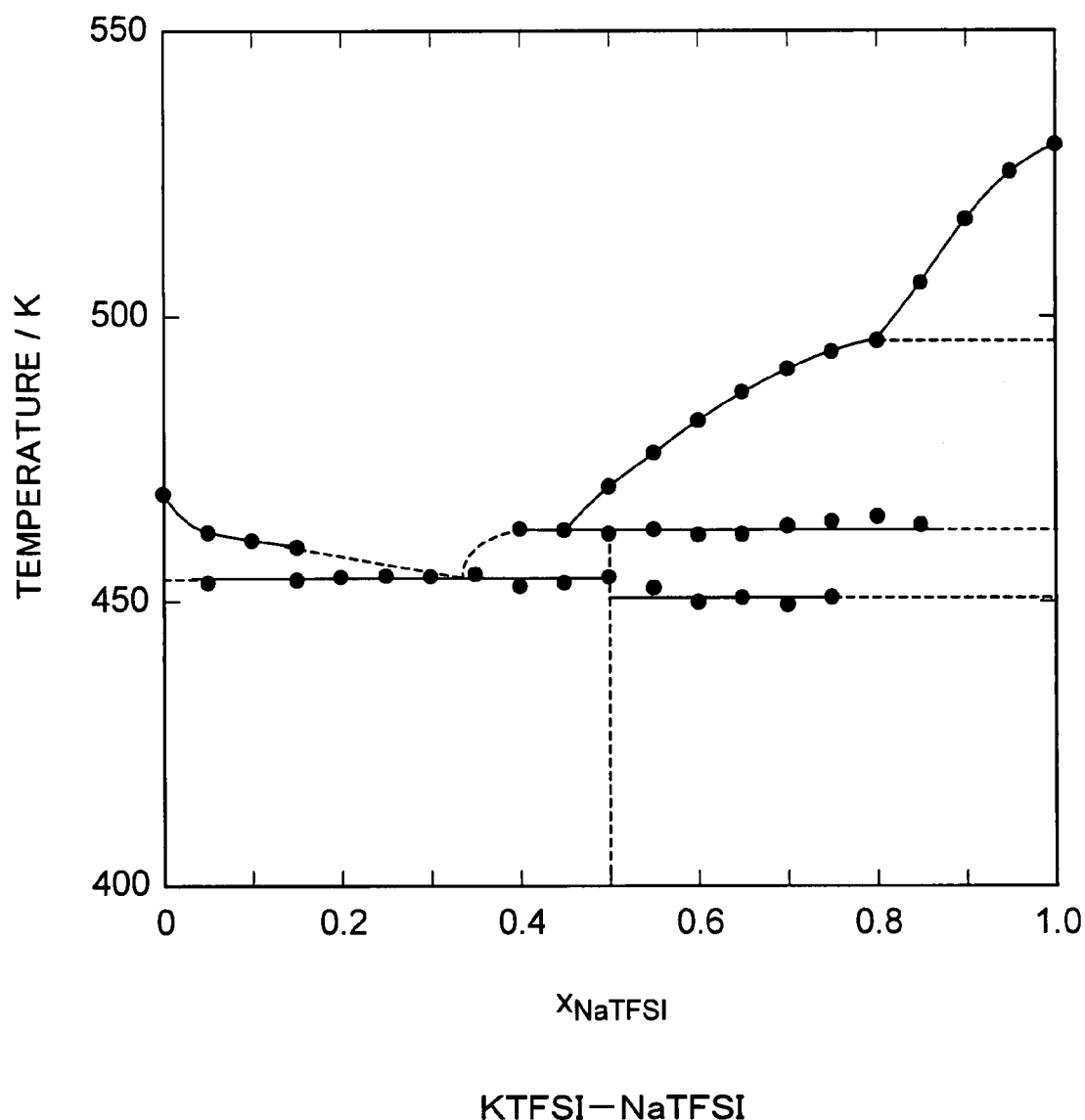
FIG. 19 is a binary system phase diagram prepared by plotting endothermic peaks of the KTFSI—NaTFSI mixed salt in Examples of the present invention.

The following shows the NaTFSI—KTFSI system. FIG. 18(a) shows an example of a DSC curve of the NaTFSI—KTFSI mixed salt, which example is obtained when $x_{NaTFSI}$=0.35. FIG. 18(b) shows an example of the DSC curve of the NaTFSI—KTFSI mixed salt, which example is obtained when $X_{NaTFSI}$=0.70. FIG. 19 shows a binary system phase diagram prepared by plotting endothermic peaks of these examples. It was found that the eutectic composition was $x_{NaTFSI}$=0.33 and the eutectic temperature was approximately 453 K, about the same as the LiTFSI—NaTFSI system. Endothermic peaks were found near approximately 463 K in a composition range where more NaTFSI is present than in the eutectic composition. Such an endothermic peak became smaller as $x_{NaTFSI}$ became larger, and was not able to be found on a DSC curve obtained when $x_{NaTFSI}$=0.80 or higher. Further, starting from approximately $x_{NaTFSI}$=0.50, the endothermic peaks found in the lowest temperature range indicated temperatures that are lower by approximately 5 K. Although this may be an error of measurement, it is considered that a compound such as NaK(TFSI) exists when $x_{NaTFSI}$=0.50.

Figure 20:
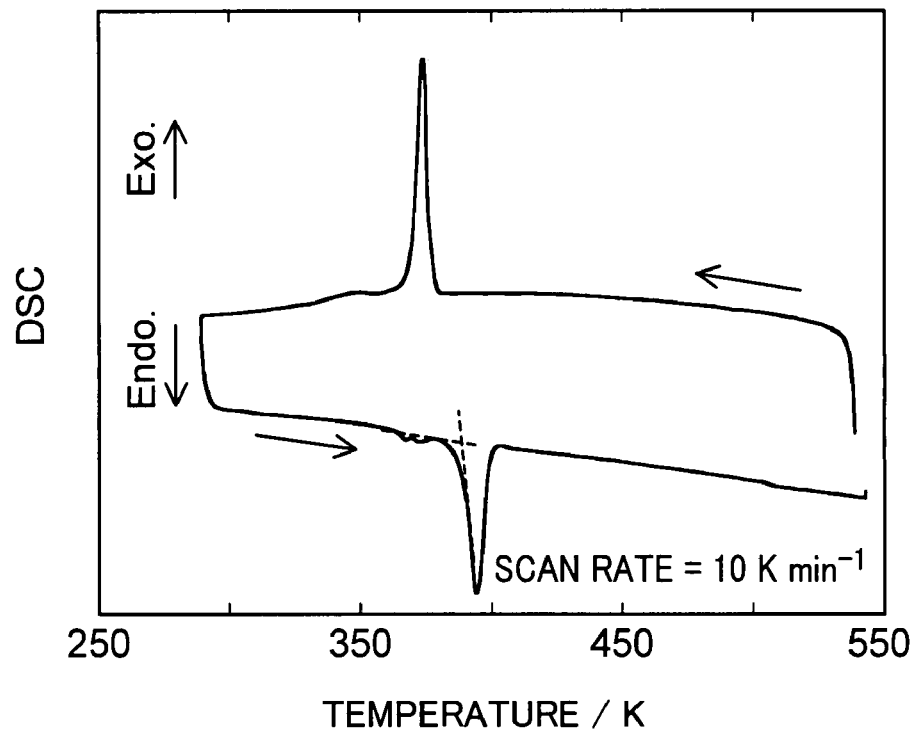
FIG. 20($a$) is a diagram showing an example of DSC curves of a NaTFSI—CsTFSI mixed salt in Examples of the present invention, which example is obtained when $x_{NaTFSI}=0.05$.
Figure 20:
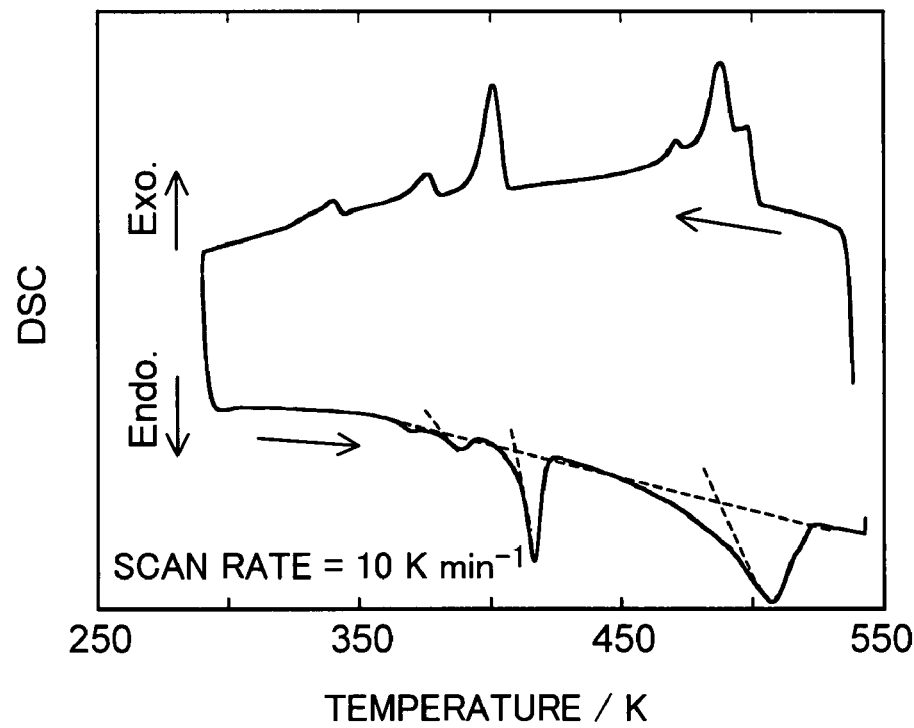
Figure 21:
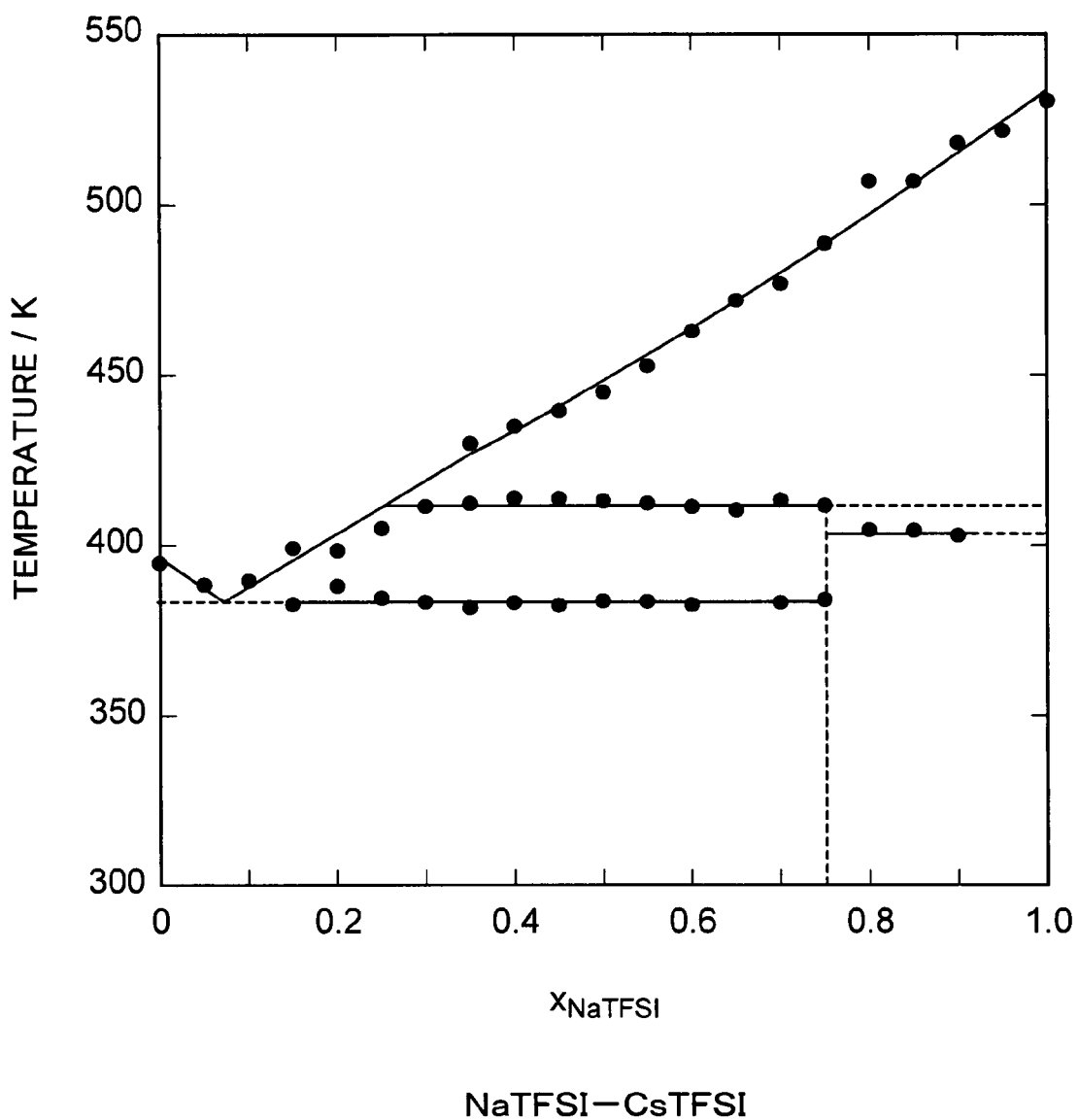
FIG. 21 is a binary system phase diagram prepared by plotting endothermic peaks of the NaTFSI—CsTFSI mixed salt in Examples of the present invention.

The following shows the NaTFSI—CsTFSI system. FIG. 20(a) shows an example of a DSC curve of the NaTFSI—CsTFSI mixed salt, which example is obtained when $x_{NaTFSI}$=0.05. FIG. 20(b) shows an example of the DSC curve of the NaTFSI—CsTFSI mixed salt, which example is obtained when $x_{NaTFSI}$=0.70. FIG. 21 shows a binary system phase diagram prepared by plotting endothermic peaks of these examples. In this case, it was found that the eutectic composition was $x_{NaTFSI}$=0.70, where a fairly large amount of CsTFSI is present, and the eutectic temperature was approximately 383 K. In this system, an endothermic peak was found near 413 K on a side where more NaTFSI is present than in the eutectic composition. However, the endothermic peak became smaller as $x_{NaTFSI}$ became larger, and was not able to be found on a DSC curve obtained when $x_{NaTFSI}$=0.80 or higher. Further, the endothermic peak found near 383 K disappeared as $x_{NaTFS1}$ became larger. Instead, an endothermic peak was found near 403 K.

In consideration of the fact that the respective melting points of KTFSI and CsTFSI are 469 K and 395 K, the melting point of the eutectic composition of each of the NaTFSI—KTFSI system and the NaTFSI—CsTFSI system approximated to the melting point of the latter salt, and was found not to be greatly lowered.

Figure 22:
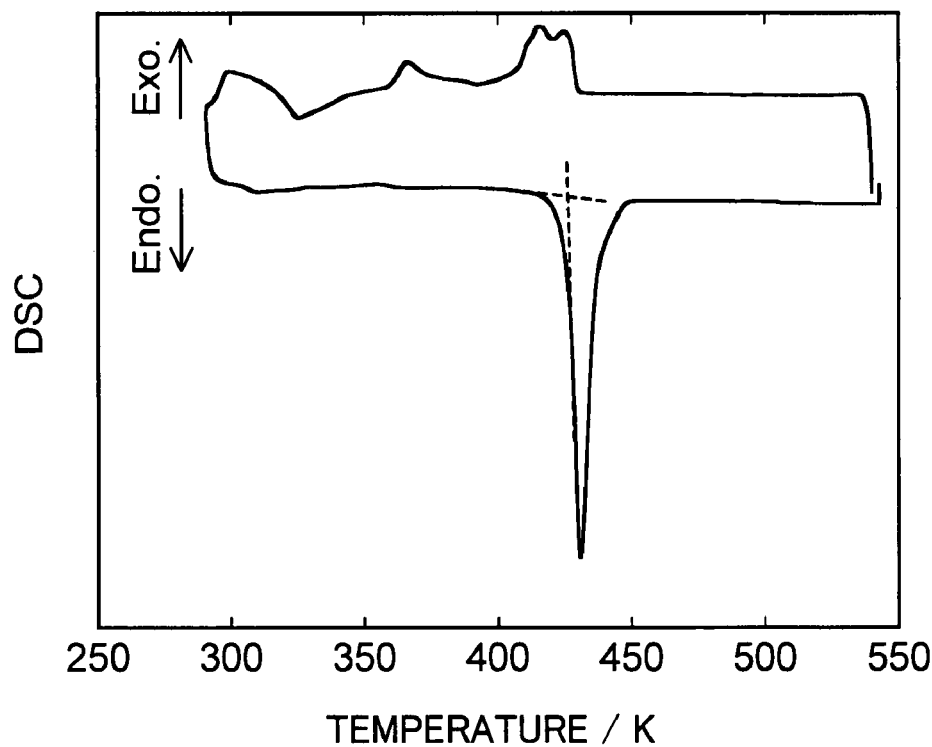
FIG. 22(a) is a diagram showing an example of DSC curves of a LiTFSI—KTFSI mixed salt in Examples of the present invention, which example is obtained when $x_{LiTFSI}=0.45$.
FIG. 22(b) is a diagram showing an example of the DSC curves of the LiTFSI—KTFSI mixed salt in Examples of the present invention, which example is obtained when $x_{LiTFSI}=0.95$.
Figure 22:
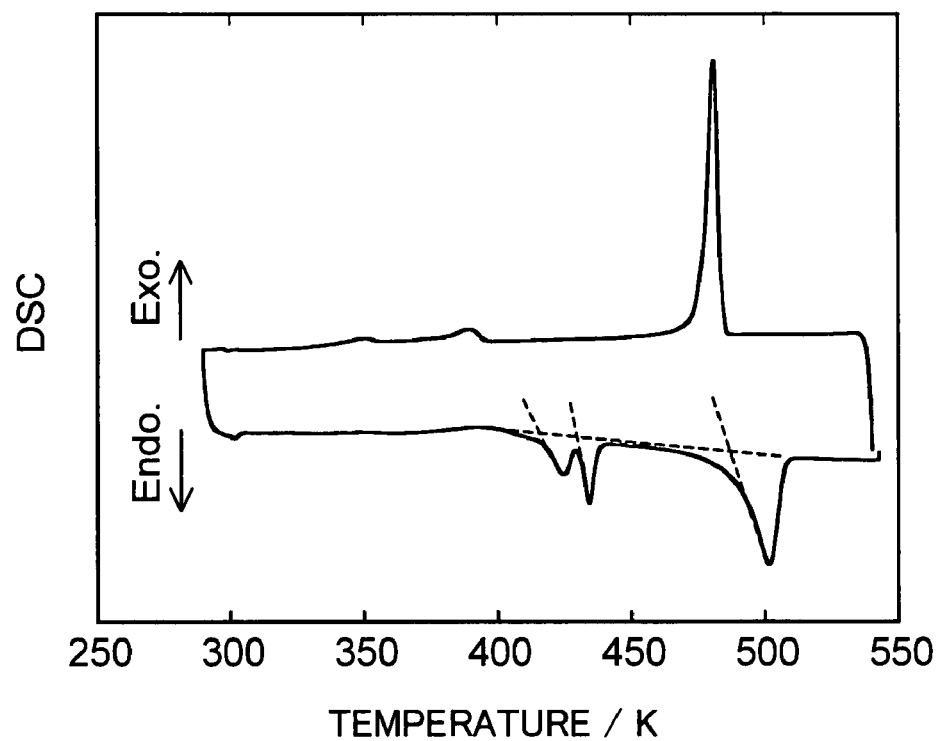

The following shows the LiTFSI—KTFSI system. FIG. 22(a) shows an example of a DSC curve of the LiTFSI—KTFSI mixed salt, which example is obtained when $x_{LiTFSI}$=0.45. FIG. 22(b) shows an example of the DSC curve of the LiTFSI—KTFSI mixed salt, which example is obtained when $x_{LiTFSI}$=0.95. FIG. 23 shows a binary system phase diagram prepared by plotting endothermic peaks of these examples. It was found that the eutectic composition was $x_{LiTFSI}$=0.43 and the eutectic temperature was approximately 423 K. Endothermic peaks were found near approximately 500 K in a composition range where more LiTFSI is present than in the eutectic composition. Further, starting from approximately $x_{LiTFSI}$=0.75, the endothermic peaks found in the lowest temperature range indicated temperatures that are lower by approximately 5 K. Although this may be an error of measurement, it is considered that a compound such as $Li_3K(TFSI)_4$ exists when $x_{LiTFSI}$=0.75.

Figure 24:
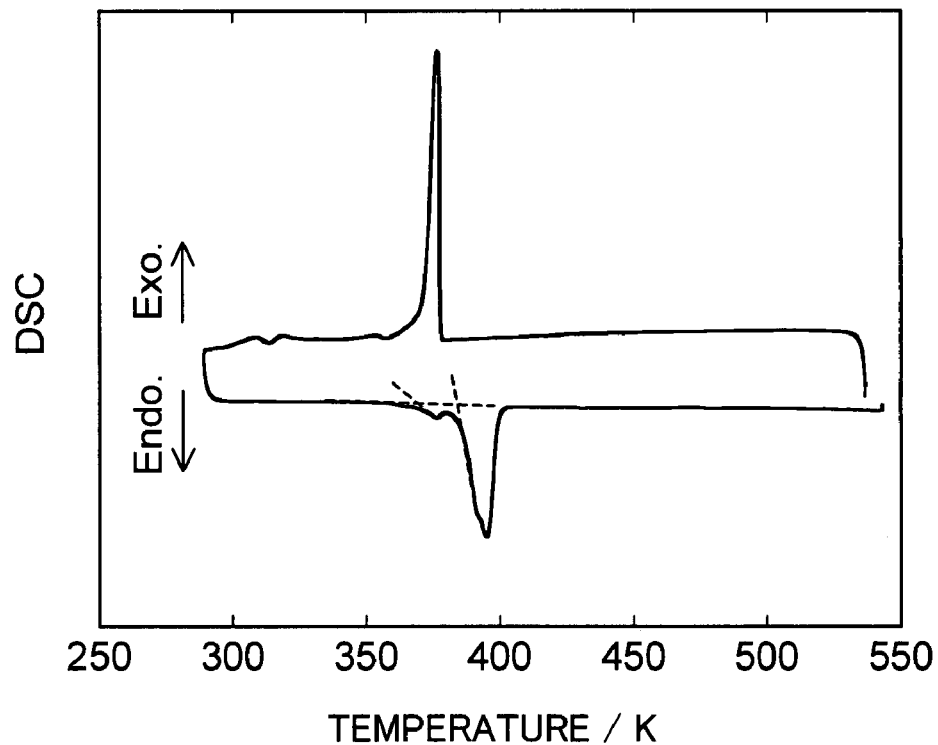
FIG. 24(a) is a diagram showing an example of DSC curves of a LiTFSI—CsTFSI mixed salt in Examples of the present invention, which example is obtained when $x_{LiTFSI}=0.05$.
FIG. 24(b) is a diagram showing an example of the DSC curves of the LiTFSI—CsTFSI mixed salt in Examples of the present invention, which example is obtained when $x_{LiTFSI}=0.40$.
Figure 24:
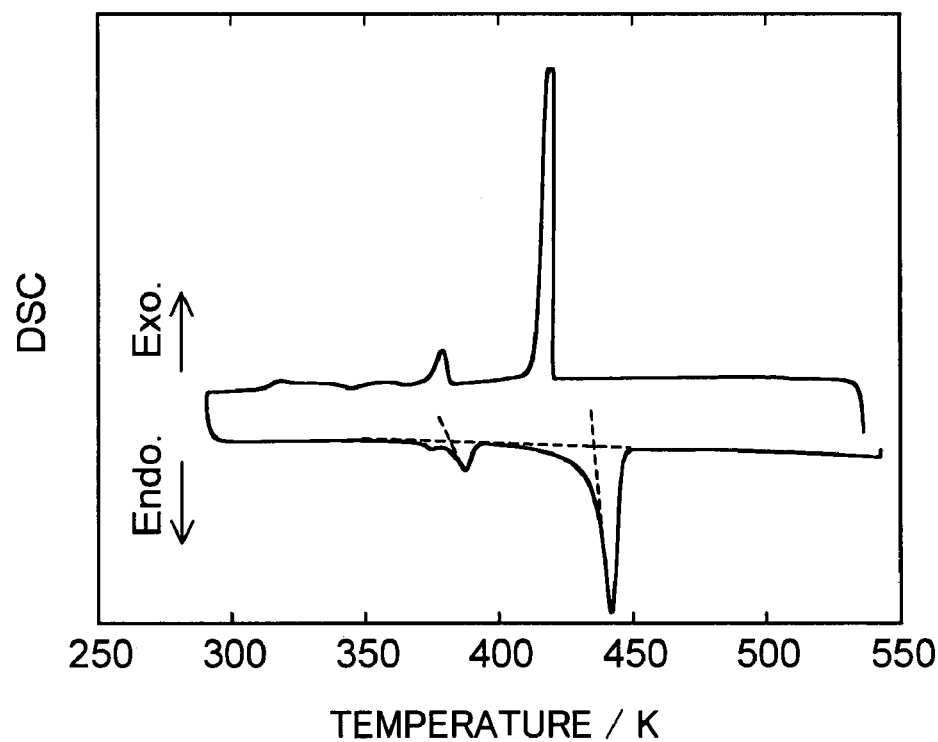
Figure 25:
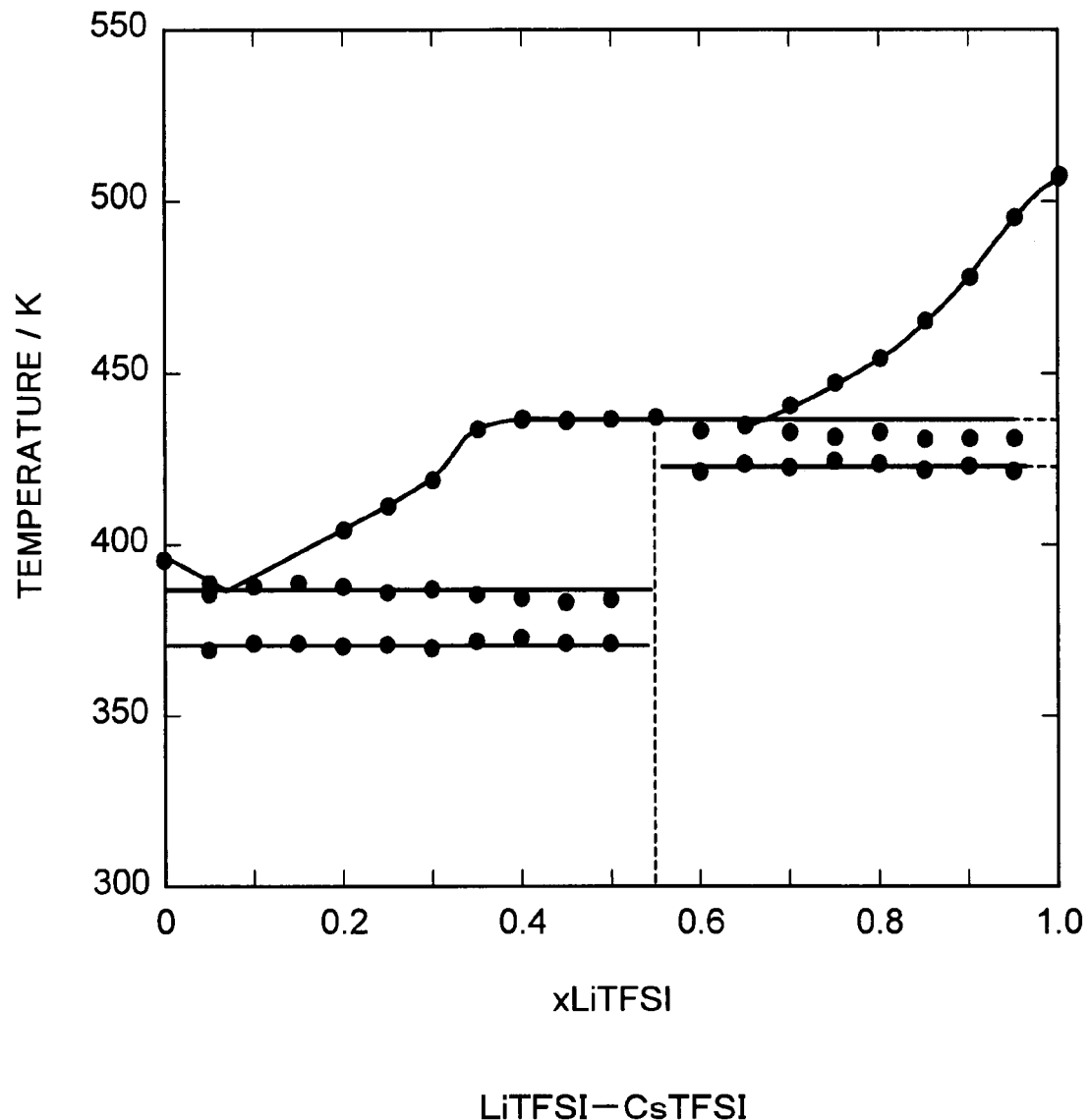
FIG. 25 is a binary system phase diagram prepared by plotting endothermic peaks of the LiTFSI—CsTFSI mixed salt in Examples of the present invention.

The following shows the LiTFSI—CsTFSI system. FIG. 24(a) shows an example of a DSC curve of the LiTFSI—CsTFSI mixed salt, which example is obtained when $x_{LiTFSI}$=0.05. FIG. 24(b) shows an example of the DSC curve of the LiTFSI—CsTFSI mixed salt, which example is obtained when $x_{LiTFSI}$=0.40. FIG. 25 shows a binary system phase diagram prepared by plotting endothermic peaks of these examples. It was found that the eutectic composition was $x_{LiTFSI}$=0.07 and the eutectic temperature was approximately 385 K. Endothermic peaks were found near approximately 445 K in a composition range where more LiTFSI is present than in the eutectic composition. Further, starting from approximately $x_{LiTFSI}$=0.55, the endothermic peaks found in the lowest temperature range indicated temperatures that are higher by approximately 50 K. Although this may be an error of measurement, it is considered that a compound such as $LiCs(TFSI)_2$ exists when $x_{LiaTFSI}$=0.5.

Figure 26:
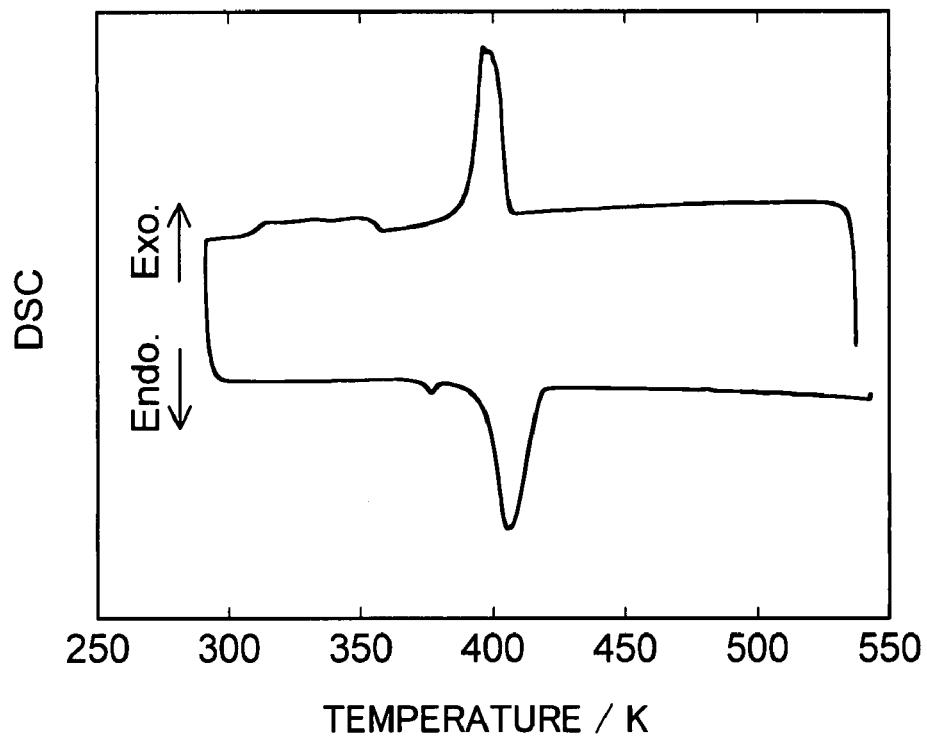
FIG. 26(a) is a diagram showing an example of DSC curves of a KTFSI—CsTFSI mixed salt in Examples of the present invention, which example is obtained when $x_{LiTFSI}=0.20$.
FIG. 26(b) is a diagram showing an example of the DSC curves of the KTFSI—CsTFSI mixed salt in Examples of the present invention, which example is obtained when $x_{LiTFSI}=0.70$.
Figure 26:
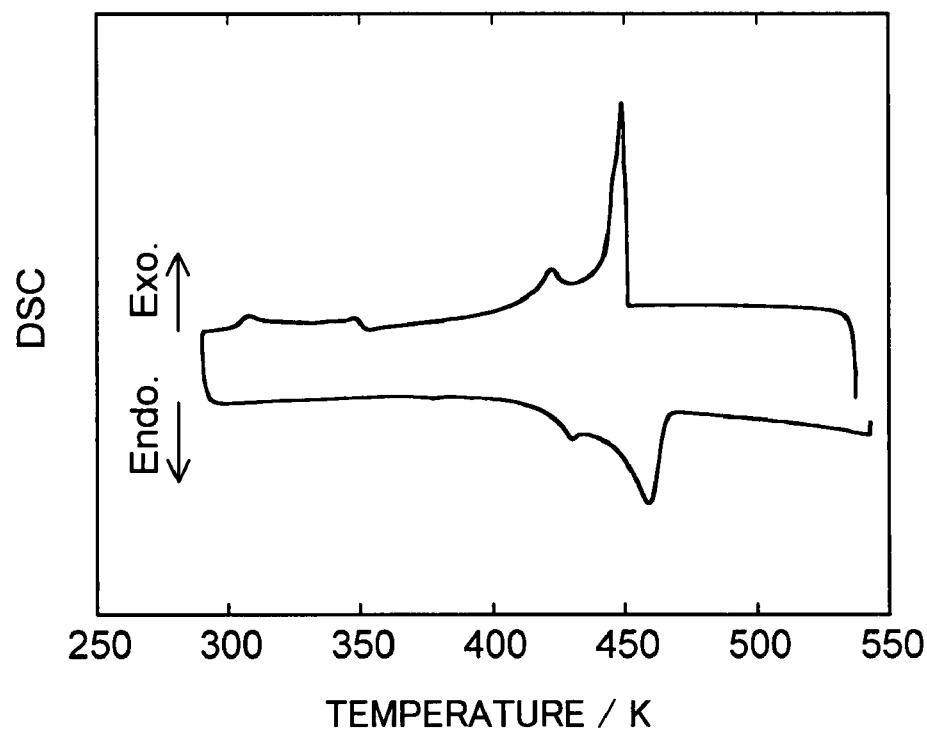
Figure 27:
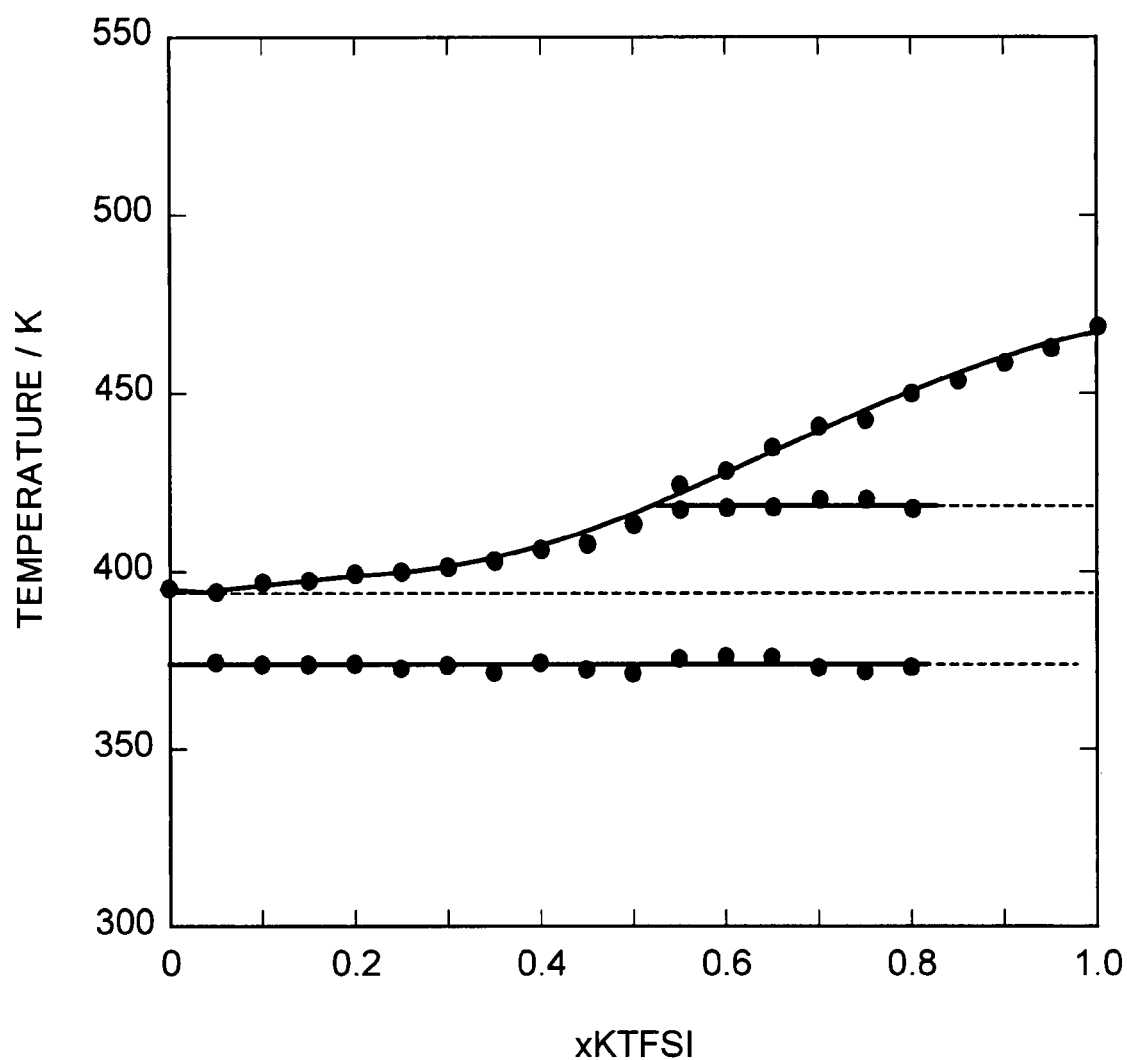
FIG. 27 is a binary system phase diagram prepared by plotting endothermic peaks of the KTFSI—CsTFSI mixed salt in Examples of the present invention.

Finally, the KTFSI—CsTFSI system is shown. FIG. 26(a) shows an example of a DSC curve of the KTFSI—CsTFSI mixed salt, which example is obtained when $x_{LiTFSI}$=0.20. FIG. 26(b) shows an example of the DSC curve of the KTFSI—CsTFSI mixed salt, which example is obtained when $x_{LiTFSI}$=0.70. FIG. 27 shows a binary system phase diagram prepared by plotting endothermic peaks of these examples. This binary system mixed salt showed no decrease in eutectic temperature. For this reason, no eutectic composition is shown. Although no eutectic point is shown, the KTFSI—CsTFSI system is an electrolyte in which $K^+$ ions are transferred at a lower temperature than in a KTFSI simple salt. Therefore, the KTFSI—CsTFSI can be used as a molten salt composition according to the present invention.

FIG. 28 shows the thermal decomposition of each salt, and FIG. 29 shows the melting point of each salt. Further, FIG. 30 shows the eutectic composition and eutectic temperature of each mixed salt. From these results, it is found that a molten salt composition obtained by mixing two types of molten salt used in Example has a much lower eutectic temperature than a simple salt does.

(3) Summary

In Examples, research was conducted on a TFSI molten salt, expected to be applied, for example, as an electrolyte liquid for use in an intermediate temperature range, whose cation is an alkali metal. As a result of thermal analysis, it was found that while the thermal decomposition temperature of a simple salt becomes higher as the size of a cation becomes larger, the melting point becomes highest in case of NaTFSI. Further, as for a mixture of NaTFSI and another salt, the LiTFSI—NaTFSI and LiTFSI—KTFSI show a most remarkable melting point depression in eutectic point. It was found that the NaTFSI—CsTFSI exhibits the lowest eutectic temperature (383 K) of all the binary system mixed salts considered in the present invention.

Further, an endothermic peak was found which is considered to correspond to a phase transition in a range of temperatures lower than the melting point. As a result of electrochemical measurement, it was found that alkali metal can be deposited on a cathode side of each simple salt. That is, it was confirmed by cyclic voltammetry that the cathodic limit is the deposition of alkali metal or an alloy thereof. However, an unknown reduction current was found at a more noble potential. This requires further consideration.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

As described above, a molten salt composition according to the present invention has a melting point that can be made lower than the melting point of a simple salt. Further, it is possible to widen, by setting the composition and proportions, the range of temperatures at which the molten salt composition according to the present invention can be used. For this reason, use of the molten salt composition according to the present invention make it possible to lower the melting point of an electrolyte, thereby bringing about advantages in terms of energy efficiency and safety. Further, the widening of the operating temperature range brings about such an advantage as a wider range of materials that are chosen to be applied to batteries and the like. Therefore, the molten salt composition according to the present invention has a wide range of industrial applicability such as plating, semiconductor, battery industry, and the like.

The invention claimed is:

1. A molten salt composition consisting essentially of two or more MTFSI molten salts whose anion is a substance TFSI represented by chemical formula (1) and whose cation is an alkali metal M

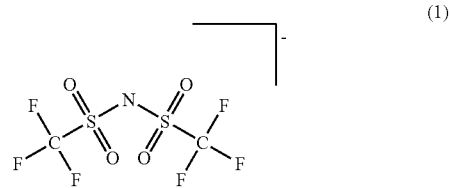

wherein two or more MTFSI molten salts are present in amounts of a eutectic composition or about a eutectic composition.

2. The molten salt composition as set forth in claim 1, wherein the molten salt MTFSI is selected from the group consisting of LiTFSI, NaTFSI, KTFSI, RbTFSI, and CsTFSI.

3. The molten salt composition as set forth in claim 1, wherein the molten salt composition is a binary system composition obtained by mixing two types of molten salt MTFSI, and is a LiTFSI—NaTFSI mixed system, a LiTFSI-KTFSI mixed system, a LiTFSI—CsTFSI mixed system, a NaTFSI-KTFSI mixed system, a NaTFSI—CsTFSI mixed system, or a KTFSI—CsTFSI mixed system.

4. An electrolyte containing a molten salt composition as set forth in claim 1.

5. A battery containing an electrolyte as set forth in claim 4.

6. The battery as set forth in claim 5, wherein the battery is used in a temperature range of 110° C. to 350° C.

7. The battery as set forth in claim 6, wherein the battery is a lithium battery, a sodium-sulfur battery, or a zebra battery.

8. A charging method comprising the step of performing charging with use of a battery as set forth in claim 5.

9. An electrodeposition method comprising the step of depositing metal or ceramics with use of an electrolyte as set forth in claim 4.

10. A film-forming method comprising the steps of:
depositing metal or ceramics with use of an electrolyte as set forth in claim 4; and
forming a film on a surface of a substance with use of the metal or ceramics thus deposited.

11. A surface-treating method comprising the steps of:
depositing metal or ceramics with use of an electrolyte as set forth in claim 4; and
treating a surface of a substance with use of the metal or ceramics thus deposited.

* * * * *